(12) United States Patent
Yip et al.

(10) Patent No.: US 6,846,323 B2
(45) Date of Patent: Jan. 25, 2005

(54) INTRAVASCULAR STENT

(75) Inventors: Philip S. Yip, San Jose, CA (US); P. H. Wilson Tsang, Sunnyvale, CA (US); Henjen Ho, San Jose, CA (US); Timothy A. Limon, Cupertino, CA (US); Svava Maria Atladottir, Sunnyvale, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 12 days.

(21) Appl. No.: 10/438,632

(22) Filed: May 15, 2003

(65) Prior Publication Data

US 2004/0230293 A1 Nov. 18, 2004

(51) Int. Cl.$^7$ .................................................. A61F 2/06
(52) U.S. Cl. .................................... 623/1.16; 623/1.17
(58) Field of Search ............................... 623/1.15, 1.16, 623/1.17, 1.18, 1.19, 1.2, 1.21, 1.22

(56) References Cited

U.S. PATENT DOCUMENTS

| | | |
|---|---|---|
| 2,836,181 A | 5/1958 | Tapp |
| 3,105,492 A | 10/1963 | Jeckel |
| 3,272,204 A | 9/1966 | Artandi et al. |
| 3,490,975 A | 1/1970 | Lightwood et al. |
| 3,509,883 A | 5/1970 | Dibelius |
| 3,526,228 A | 9/1970 | Lyng |
| 3,562,820 A | 2/1971 | Braun |
| 3,635,215 A | 1/1972 | Shea et al. |
| 3,657,744 A | 4/1972 | Ersek |
| 3,771,526 A | 11/1973 | Rudie |
| 3,868,956 A | 3/1975 | Alfidi et al. |
| 3,993,078 A | 11/1976 | Bergentz et al. |
| 4,078,167 A | 3/1978 | Banas et al. |
| 4,127,761 A | 11/1978 | Pauley et al. |
| 4,130,904 A | 12/1978 | Whalen |

(List continued on next page.)

FOREIGN PATENT DOCUMENTS

| | | |
|---|---|---|
| DE | 195 37 872 | 4/1997 |
| DE | 297 08 879 | 9/1997 |
| EP | 0 201 466 | 11/1986 |
| EP | 0 372 789 | 6/1990 |
| EP | 0 540 290 | 5/1993 |
| EP | 0 541 443 | 5/1993 |
| EP | 0 606 165 | 7/1994 |
| EP | 0 688 545 | 12/1995 |
| EP | 0 800 801 | 10/1997 |
| EP | 0 806 190 | 11/1997 |
| EP | 0 669 114 | 6/1998 |
| EP | 0 888 757 | 1/1999 |
| EP | 1 042 997 | 10/2000 |
| EP | 1 088 528 | 4/2001 |
| EP | 0 888 093 | 7/2001 |

(List continued on next page.)

OTHER PUBLICATIONS

U.S. App. No. 10/173,310 (issue fee paid Aug. 21, 2003).

*Primary Examiner*—David H. Willse
*Assistant Examiner*—Thomas J. Sweet
(74) *Attorney, Agent, or Firm*—Fulwider Patton Lee & Utecht, LLP

(57) ABSTRACT

An intravascular stent assembly for implantation in a body vessel, such as a coronary artery, includes undulating circumferential rings having peaks on the proximal end and valleys on the distal end. Adjacent rings are coupled together by links. The rings and links are arranged so that the stent has good conformability as it traverses through, or is deployed in, a tortuous body lumen. The stent is also configured such that the likelihood of peaks and valleys on adjacent rings which point directly at each other to overlap in tortuous body vessels is reduced.

35 Claims, 19 Drawing Sheets

U.S. PATENT DOCUMENTS

| | | |
|---|---|---|
| 4,140,126 A | 2/1979 | Choudhury |
| 4,141,364 A | 2/1979 | Schultze |
| 4,164,045 A | 8/1979 | Bokros et al. |
| 4,214,587 A | 7/1980 | Sakura, Jr. |
| 4,241,146 A | 12/1980 | Sivachenko et al. |
| 4,300,244 A | 11/1981 | Bokros |
| 4,313,231 A | 2/1982 | Koyamada |
| 4,319,363 A | 3/1982 | Ketharanathan |
| 4,425,908 A | 1/1984 | Simon |
| 4,441,215 A | 4/1984 | Kaster |
| 4,470,407 A | 9/1984 | Hussein |
| 4,501,264 A | 2/1985 | Rockey |
| 4,503,569 A | 3/1985 | Dotter |
| 4,512,338 A | 4/1985 | Balko |
| 4,535,770 A | 8/1985 | Lemole |
| 4,550,447 A | 11/1985 | Seiler, Jr. et al. |
| 4,553,545 A | 11/1985 | Maass et al. |
| 4,560,374 A | 12/1985 | Hammerslag |
| 4,580,568 A | 4/1986 | Gianturco |
| 4,597,389 A | 7/1986 | Ibrahim et al. |
| 4,647,416 A | 3/1987 | Seiler, Jr. et al. |
| 4,649,922 A | 3/1987 | Wiktor |
| 4,655,771 A | 4/1987 | Wallsten |
| 4,655,776 A | 4/1987 | Lesinski |
| 4,665,906 A | 5/1987 | Jervis |
| 4,665,918 A | 5/1987 | Garza et al. |
| 4,681,110 A | 7/1987 | Wiktor |
| 4,693,721 A | 9/1987 | Ducheyne |
| 4,725,334 A | 2/1988 | Brimm |
| 4,728,328 A | 3/1988 | Hughes et al. |
| 4,733,665 A | 3/1988 | Palmaz |
| 4,739,762 A | 4/1988 | Palmaz |
| 4,740,207 A | 4/1988 | Kreamer |
| 4,760,849 A | 8/1988 | Kropf |
| 4,762,128 A | 8/1988 | Rosenbluth |
| 4,768,507 A | 9/1988 | Fischel et al. |
| 4,769,029 A | 9/1988 | Patel |
| 4,771,773 A | 9/1988 | Kropf |
| 4,776,337 A | 10/1988 | Palmaz |
| 4,787,899 A | 11/1988 | Lazarus |
| 4,795,458 A | 1/1989 | Regan |
| 4,795,465 A | 1/1989 | Marten |
| 4,800,882 A | 1/1989 | Gianturco |
| 4,820,298 A | 4/1989 | Leveen et al. |
| 4,830,003 A | 5/1989 | Wolff et al. |
| 4,842,575 A | 6/1989 | Hoffman et al. |
| 4,848,343 A | 7/1989 | Wallstent et al. |
| 4,851,009 A | 7/1989 | Pinchuk |
| 4,856,516 A | 8/1989 | Hillstead |
| 4,872,874 A | 10/1989 | Taheri |
| 4,877,030 A | 10/1989 | Beck et al. |
| 4,878,906 A | 11/1989 | Lindemann et al. |
| 4,886,062 A | 12/1989 | Wiktor |
| 4,893,623 A | 1/1990 | Rosenbluth |
| 4,913,141 A | 4/1990 | Hillstead |
| 4,922,905 A | 5/1990 | Strecker |
| 4,950,227 A | 8/1990 | Savin et al. |
| 4,950,258 A | 8/1990 | Kawai et al. |
| 4,986,831 A | 1/1991 | King et al. |
| 4,994,071 A | 2/1991 | MacGregor |
| 5,015,253 A | 5/1991 | MacGregor |
| 5,019,090 A | 5/1991 | Pinchuk |
| 5,035,706 A | 7/1991 | Gianturco et al. |
| 5,037,392 A | 8/1991 | Hillstead |
| 5,059,211 A | 10/1991 | Stack et al. |
| 5,064,435 A | 11/1991 | Porter |
| 5,071,407 A | 12/1991 | Termin et al. |
| 5,089,005 A | 2/1992 | Harada |
| 5,092,877 A | 3/1992 | Pinchuk |
| 5,102,417 A | 4/1992 | Palmaz |
| 5,104,399 A | 4/1992 | Lazarus |
| 5,104,404 A | 4/1992 | Wolff |
| 5,108,415 A | 4/1992 | Pinchuk et al. |
| 5,108,417 A | 4/1992 | Sawyer |
| 5,122,154 A | 6/1992 | Rhodes |
| 5,133,732 A | 7/1992 | Wiktor |
| 5,135,536 A | 8/1992 | Hillstead |
| 5,139,480 A | 8/1992 | Hickle et al. |
| 5,147,385 A | 9/1992 | Beck et al. |
| 5,147,400 A | 9/1992 | Kaplan et al. |
| 5,158,548 A | 10/1992 | Lau et al. |
| 5,163,952 A | 11/1992 | Froix |
| 5,195,984 A | 3/1993 | Schatz |
| 5,197,978 A | 3/1993 | Hess |
| 5,217,483 A | 6/1993 | Tower |
| 5,226,913 A | 7/1993 | Pinchuk |
| 5,282,823 A | 2/1994 | Schwartz et al. |
| 5,282,824 A | 2/1994 | Gianturco |
| 5,292,331 A | 3/1994 | Boneau |
| 5,304,200 A | 4/1994 | Spaulding |
| 5,344,425 A | 9/1994 | Sawyer |
| 5,354,308 A | 10/1994 | Simon et al. |
| 5,354,309 A | 10/1994 | Schnepp-Pesch et al. |
| 5,356,423 A | 10/1994 | Tibon et al. |
| 5,366,504 A | 11/1994 | Andersen et al. |
| 5,383,892 A | 1/1995 | Cardon et al. |
| 5,389,106 A | 2/1995 | Tower |
| 5,395,390 A | 3/1995 | Simon et al. |
| 5,405,377 A | 4/1995 | Cragg |
| 5,413,597 A | 5/1995 | Krajicek |
| 5,421,955 A | 6/1995 | Lau et al. |
| 5,449,373 A | 9/1995 | Pinchasik et al. |
| 5,476,506 A | 12/1995 | Lunn |
| 5,514,154 A | 5/1996 | Lau et al. |
| 5,527,324 A | 6/1996 | Krantz et al. |
| 5,545,210 A | 8/1996 | Hess et al. |
| 5,549,663 A | 8/1996 | Cottone, Jr. |
| 5,554,181 A | 9/1996 | Das |
| 5,569,295 A | 10/1996 | Lam |
| 5,591,197 A | 1/1997 | Orth et al. |
| 5,601,593 A | 2/1997 | Freitag |
| 5,607,442 A | 3/1997 | Fischell et al. |
| 5,630,829 A | 5/1997 | Lauterjung |
| 5,632,771 A | 5/1997 | Boatman et al. |
| 5,636,641 A | 6/1997 | Fariabi |
| 5,643,312 A | 7/1997 | Fischell et al. |
| 5,653,727 A | 8/1997 | Wiktor |
| 5,669,932 A | 9/1997 | Fischell et al. |
| 5,674,241 A | 10/1997 | Bley et al. |
| 5,674,278 A | 10/1997 | Boneau |
| 5,681,346 A | 10/1997 | Orth et al. |
| 5,693,089 A | 12/1997 | Inoue |
| 5,697,971 A | 12/1997 | Fischell et al. |
| 5,421,154 A | 1/1998 | Lau et al. |
| 5,707,386 A | 1/1998 | Schnepp-Pesch et al. |
| 5,707,388 A | 1/1998 | Lauterjung |
| 5,716,393 A | 2/1998 | Lindenberg et al. |
| 5,725,572 A | 3/1998 | Lam et al. |
| 5,733,303 A | 3/1998 | Israel et al. |
| 5,741,327 A | 4/1998 | Frantzen |
| 5,755,781 A | 5/1998 | Jayaraman |
| 5,759,192 A | 6/1998 | Saunders |
| 5,776,161 A | 7/1998 | Globerman |
| 5,800,521 A | 9/1998 | Orth |
| 5,810,868 A | 9/1998 | Lashinski et al. |
| 5,810,872 A | 9/1998 | Kanesaka |
| 5,824,040 A | 10/1998 | Cox et al. |
| 5,827,321 A | 10/1998 | Roubin et al. |
| 5,836,964 A | 11/1998 | Richter et al. |
| 5,836,966 A | 11/1998 | St. Germain |
| 5,843,120 A | 12/1998 | Israel et al. |

| Patent Number | Date | Name |
|---|---|---|
| 5,843,175 A | 12/1998 | Frantzen |
| 5,843,419 A | 12/1998 | Imran |
| 5,868,781 A | 2/1999 | Killion |
| 5,868,783 A | 2/1999 | Tower |
| 5,876,449 A | 3/1999 | Starck et al. |
| 5,879,370 A | 3/1999 | Fischell et al. |
| 5,879,382 A | 3/1999 | Boneau |
| 5,893,887 A | 4/1999 | Jayaraman |
| 5,911,754 A | 6/1999 | Kanesaka et al. |
| 5,913,895 A | 6/1999 | Burpee et al. |
| 5,922,005 A | 7/1999 | Richter et al. |
| 5,922,020 A | 7/1999 | Klein et al. |
| 5,925,061 A | 7/1999 | Ogi et al. |
| 5,931,866 A | 8/1999 | Frantzen |
| 5,935,161 A | 8/1999 | Robinson et al. |
| 5,935,162 A | 8/1999 | Dang |
| 5,938,682 A | 8/1999 | Hojeibane et al. |
| 5,938,697 A | 8/1999 | Killion et al. |
| 5,948,016 A | 9/1999 | Jang |
| 5,954,743 A | 9/1999 | Jang |
| 5,964,798 A | 10/1999 | Imran |
| 5,967,986 A | 10/1999 | Cimochowski et al. |
| 5,968,093 A | 10/1999 | Kranz |
| 5,972,018 A | 10/1999 | Israel et al. |
| 5,980,552 A | 11/1999 | Pinchasik et al. |
| 5,993,489 A | 11/1999 | Lewis et al. |
| 6,001,125 A | 12/1999 | Golds et al. |
| 6,004,348 A | 12/1999 | Banas et al. |
| 6,013,091 A | 1/2000 | Ley et al. |
| 6,017,365 A | 1/2000 | Von Oepen |
| 6,019,789 A | 2/2000 | Dinh et al. |
| 6,022,371 A | 2/2000 | Killion |
| 6,022,374 A | 2/2000 | Imran |
| 6,033,433 A | 3/2000 | Ehr et al. |
| 6,033,435 A | 3/2000 | Penn et al. |
| 6,039,755 A | 3/2000 | Edwin et al. |
| 6,039,756 A | 3/2000 | Jang |
| 6,042,597 A | 3/2000 | Kveen et al. |
| 6,042,606 A | 3/2000 | Frantzen |
| 6,048,361 A | 4/2000 | Von Oepen |
| 6,051,020 A | 4/2000 | Goicoechia et al. |
| 6,053,940 A | 4/2000 | Wijay |
| 6,053,941 A | 4/2000 | Lindenberg et al. |
| 6,053,943 A | 4/2000 | Edwin et al. |
| 6,056,775 A | 5/2000 | Borghi et al. |
| 6,059,822 A | 5/2000 | Kanesaka et al. |
| 6,063,113 A | 5/2000 | Kavltcladze et al. |
| 6,066,168 A | 5/2000 | Lau et al. |
| 6,066,169 A | 5/2000 | McGuinness |
| 6,068,656 A | 5/2000 | Von Oepen |
| 6,071,298 A | 6/2000 | Lashinski et al. |
| 6,077,297 A | 6/2000 | Robinson et al. |
| 6,080,191 A | 6/2000 | Summers |
| 6,083,259 A | 7/2000 | Frantzen |
| 6,086,604 A | 7/2000 | Fischell et al. |
| 6,086,611 A | 7/2000 | Duffy et al. |
| 6,090,127 A | 7/2000 | Globerman |
| 6,093,199 A | 7/2000 | Brown et al. |
| 6,093,203 A | 7/2000 | Uflacker |
| 6,099,455 A | 8/2000 | Columbo et al. |
| 6,099,559 A | 8/2000 | Nolting |
| 6,099,560 A | 8/2000 | Penn et al. |
| 6,099,561 A | 8/2000 | Alt |
| 6,102,940 A | 8/2000 | Robichon et al. |
| 6,106,548 A | 8/2000 | Roubin et al. |
| 6,113,627 A | 9/2000 | Jang |
| 6,113,628 A | 9/2000 | Borghi |
| 6,117,165 A | 9/2000 | Becker |
| 6,123,721 A | 9/2000 | Jang |
| 6,129,754 A | 10/2000 | Kanesaka et al. |
| 6,129,755 A | 10/2000 | Mathis et al. |
| 6,149,682 A | 11/2000 | Frid |
| 6,152,957 A | 11/2000 | Jang |
| 6,156,052 A | 12/2000 | Richter et al. |
| 6,162,243 A | 12/2000 | Gray et al. |
| 6,179,868 B1 | 1/2001 | Burpee et al. |
| 6,183,506 B1 | 2/2001 | Penn et al. |
| 6,187,034 B1 | 2/2001 | Frantzen |
| 6,190,403 B1 | 2/2001 | Fischell et al. |
| 6,200,334 B1 | 3/2001 | Jang |
| 6,206,916 B1 | 3/2001 | Furst |
| 6,217,608 B1 | 4/2001 | Penn et al. |
| 6,231,598 B1 | 5/2001 | Berry et al. |
| 6,241,762 B1 | 6/2001 | Shanley |
| 6,245,101 B1 | 6/2001 | Drasler et al. |
| 6,258,116 B1 | 7/2001 | Hojeibane |
| 6,264,688 B1 | 7/2001 | Herklotz et al. |
| 6,309,414 B1 | 10/2001 | Rolando et al. |
| 6,325,821 B1 | 12/2001 | Gaschino et al. |
| 6,330,884 B1 | 12/2001 | Kim |
| 6,342,067 B1 | 1/2002 | Mathis et al. |
| 6,348,065 B1 | 2/2002 | Brown et al. |
| 6,375,677 B1 | 4/2002 | Penn et al. |
| 6,451,049 B2 | 9/2002 | Vallana et al. |
| 6,478,816 B1 | 11/2002 | Kveen et al. |
| 6,480,315 B1 | 11/2002 | Brown |
| 6,497,723 B1 | 12/2002 | Starck et al. |
| 6,540,775 B1 | 4/2003 | Fischell et al. |
| 2001/0044649 A1 | 11/2001 | Vallana |
| 2001/0044652 A1 | 11/2001 | Moore |
| 2002/0007212 A1 * | 1/2002 | Brown et al. ............... 623/1.16 |
| 2002/0023843 A1 | 2/2002 | Cherkes |
| 2002/0032478 A1 | 3/2002 | Boekstegers et al. |
| 2002/0045933 A1 | 4/2002 | Jang |
| 2002/0045934 A1 | 4/2002 | Jang |
| 2002/0045935 A1 | 4/2002 | Jang |
| 2002/0055770 A1 * | 5/2002 | Doran et al. ............... 623/1.15 |
| 2002/0058989 A1 | 5/2002 | Chen et al. |
| 2002/0058990 A1 | 5/2002 | Jang |
| 2002/0072792 A1 | 6/2002 | Burgermeister et al. |
| 2002/0111672 A1 | 8/2002 | Kim et al. |
| 2002/0123797 A1 | 9/2002 | Majercak |
| 2003/0040790 A1 | 2/2003 | Furst |

FOREIGN PATENT DOCUMENTS

| | | |
|---|---|---|
| JP | 11-104246 | 4/1999 |
| WO | WO 94/17754 | 8/1994 |
| WO | WO 95/33422 | 12/1995 |
| WO | WO 96/03092 | 2/1996 |
| WO | W0 96/09013 | 3/1996 |
| WO | WO 97/32543 | 9/1997 |
| WO | WO 98/22159 | 5/1998 |
| WO | WO 98/58600 | 12/1998 |
| WO | WO 99/02105 | 1/1999 |
| WO | WO 99/17680 | 4/1999 |
| WO | WO 00/30563 | 6/2000 |
| WO | WO 00/42945 | 7/2000 |
| WO | WO 00/42946 | 7/2000 |
| WO | WO 02/2411 | 3/2002 |

* cited by examiner

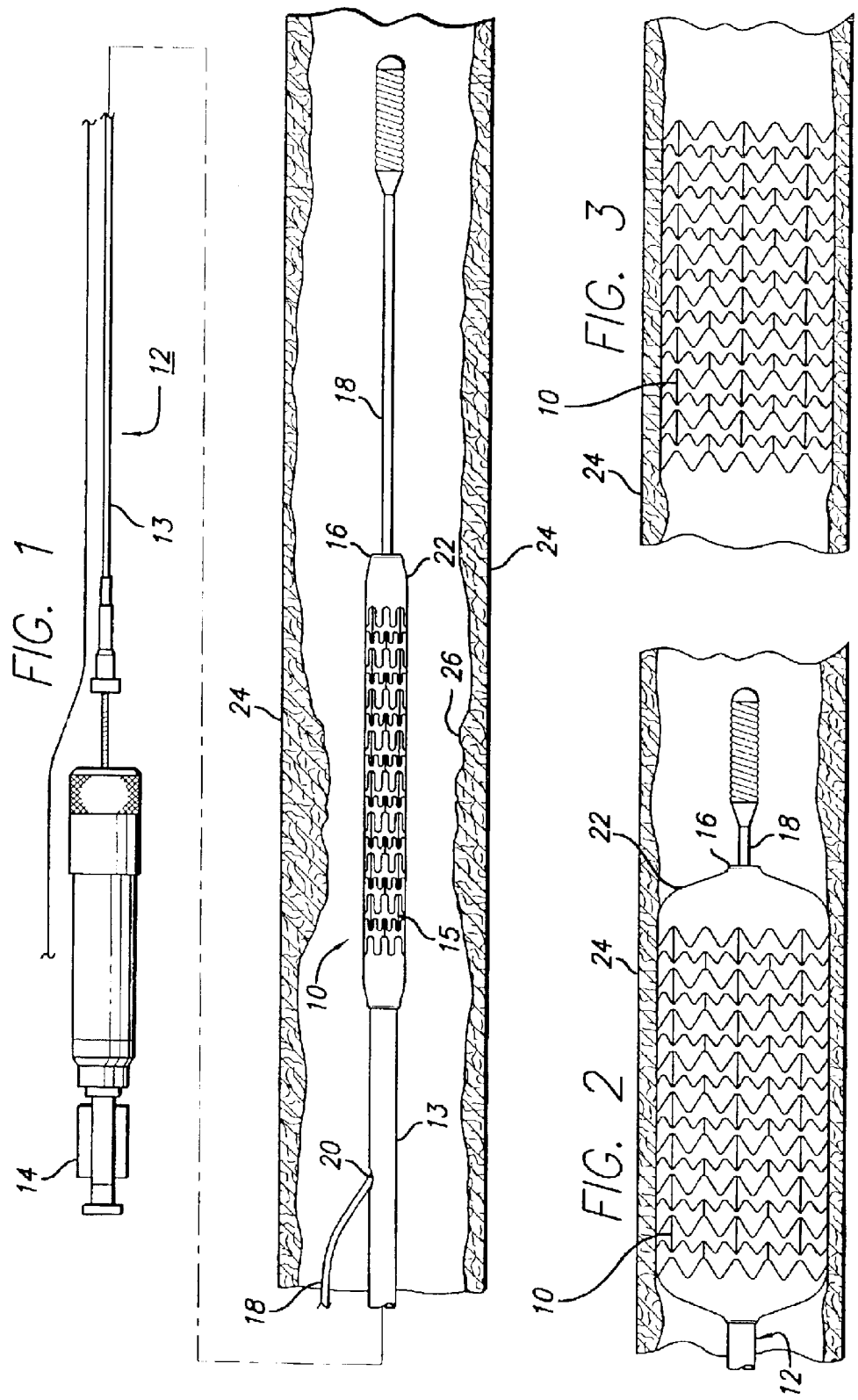

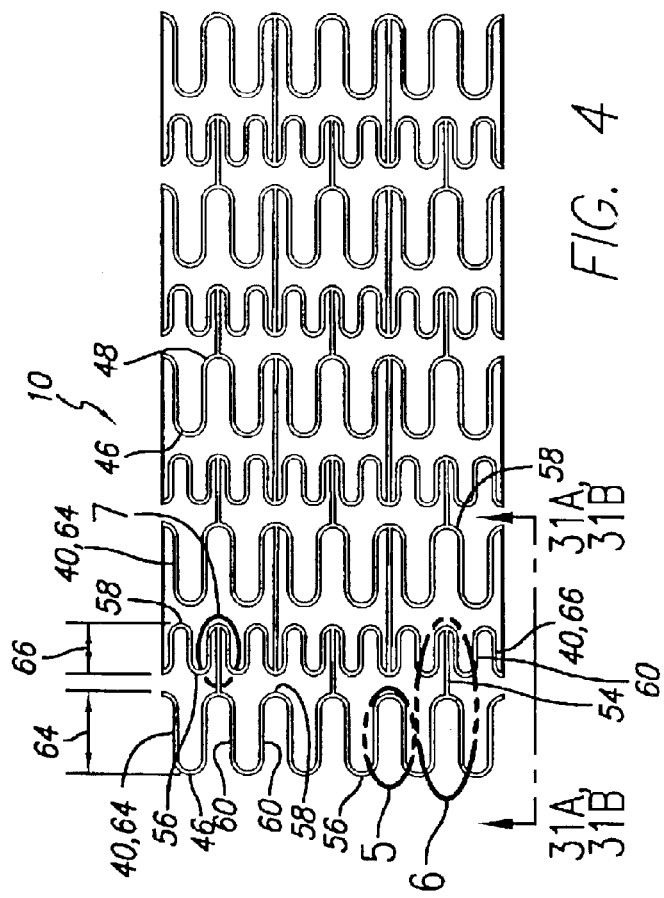
FIG. 4
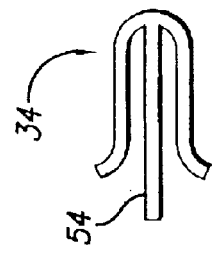
FIG. 7
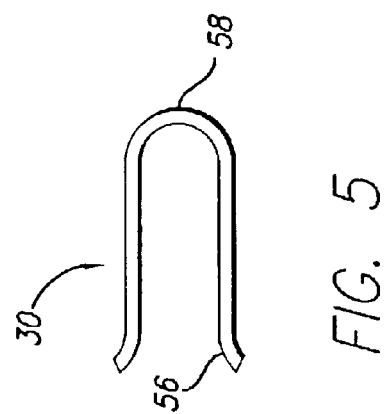
FIG. 5
FIG. 6

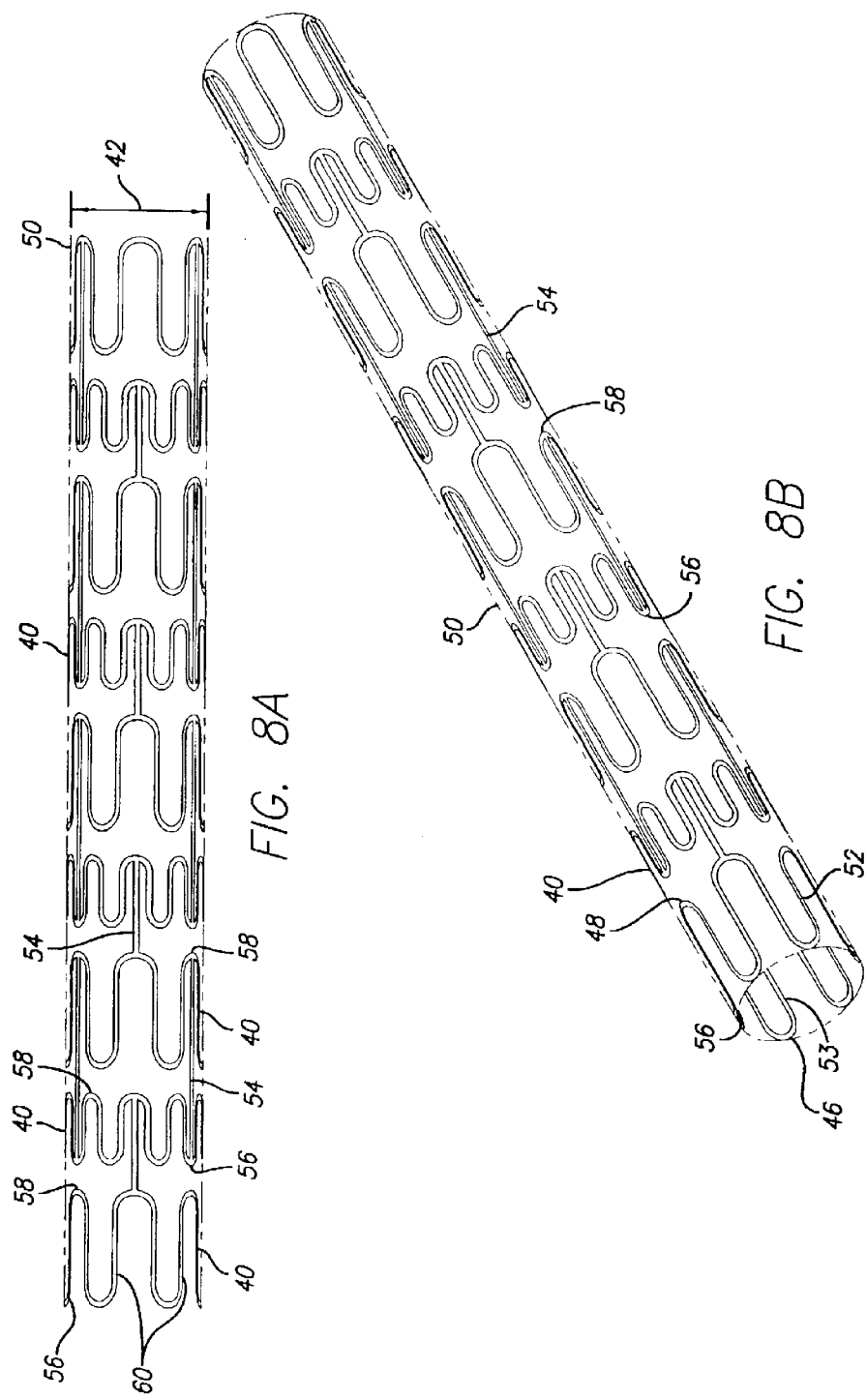

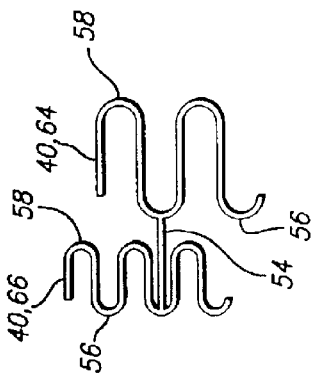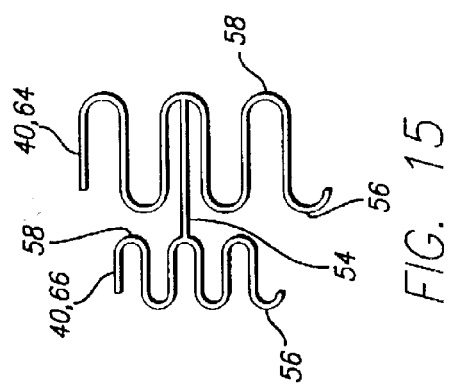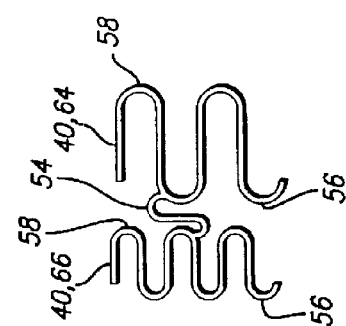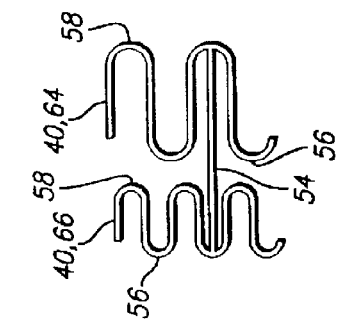

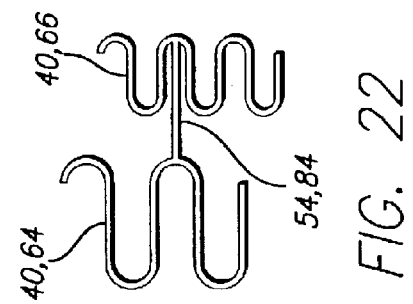
FIG. 18
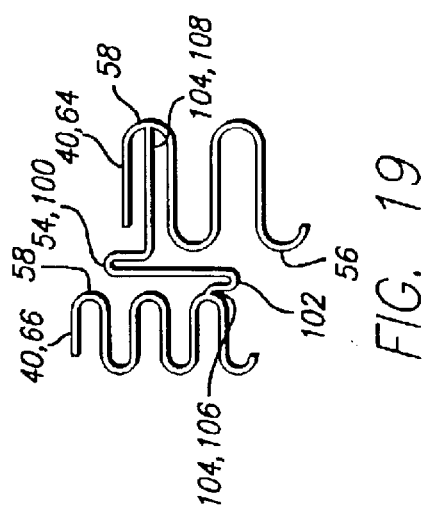
FIG. 19
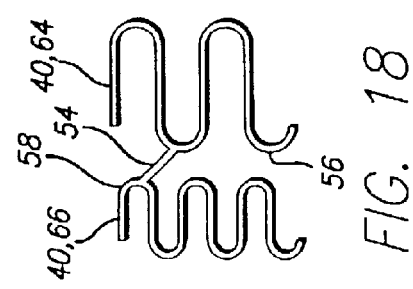
FIG. 22
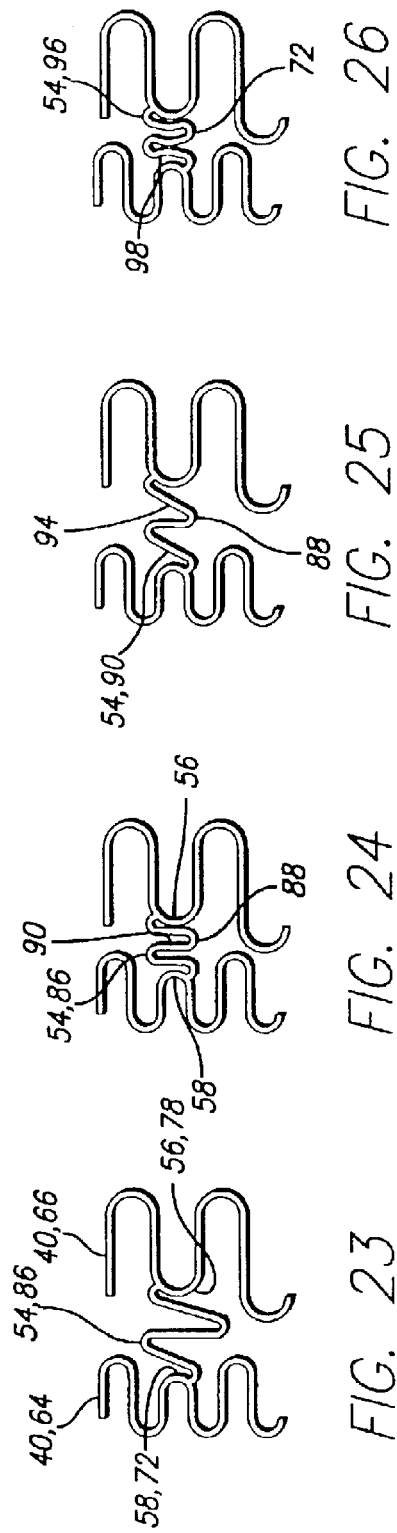
FIG. 23
FIG. 24
FIG. 25
FIG. 26

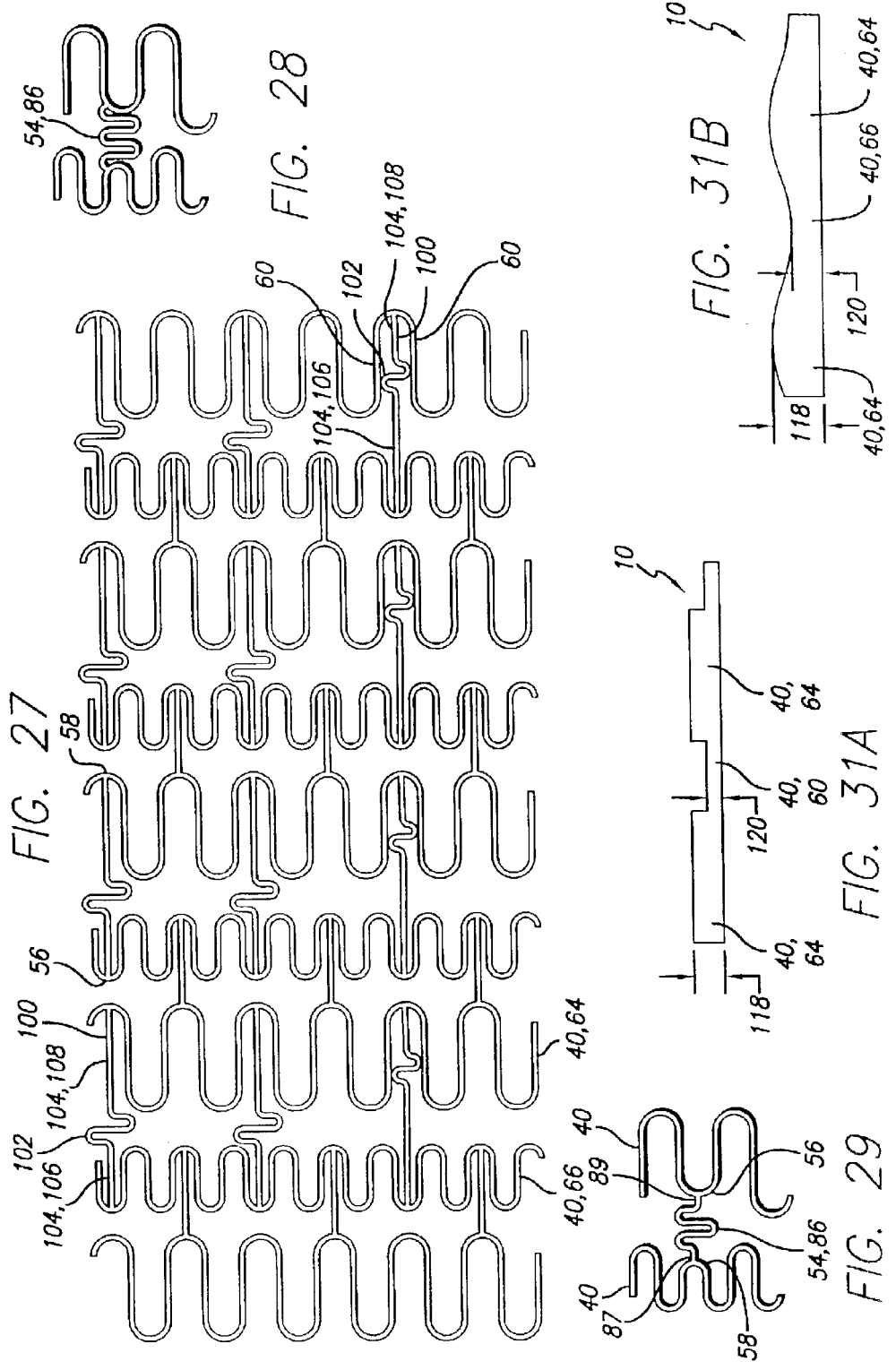

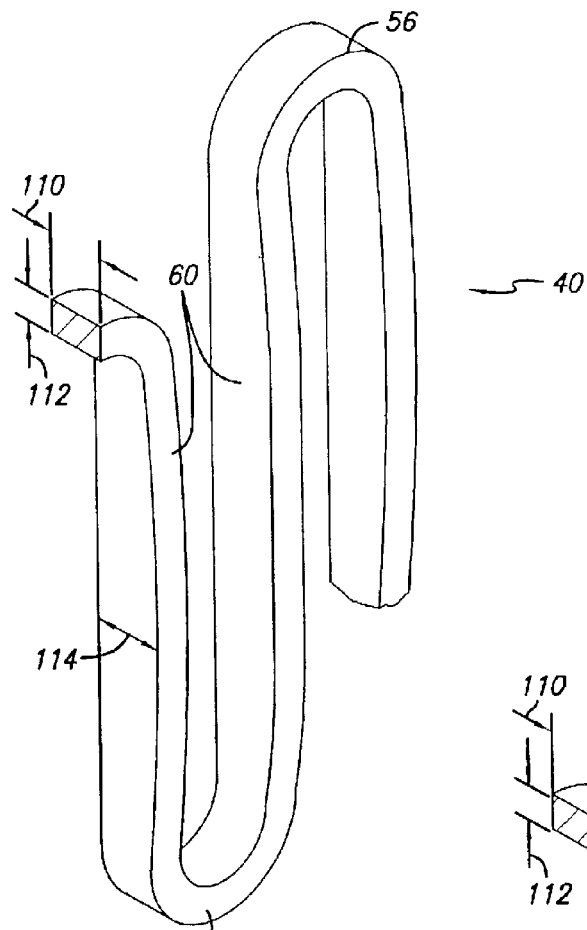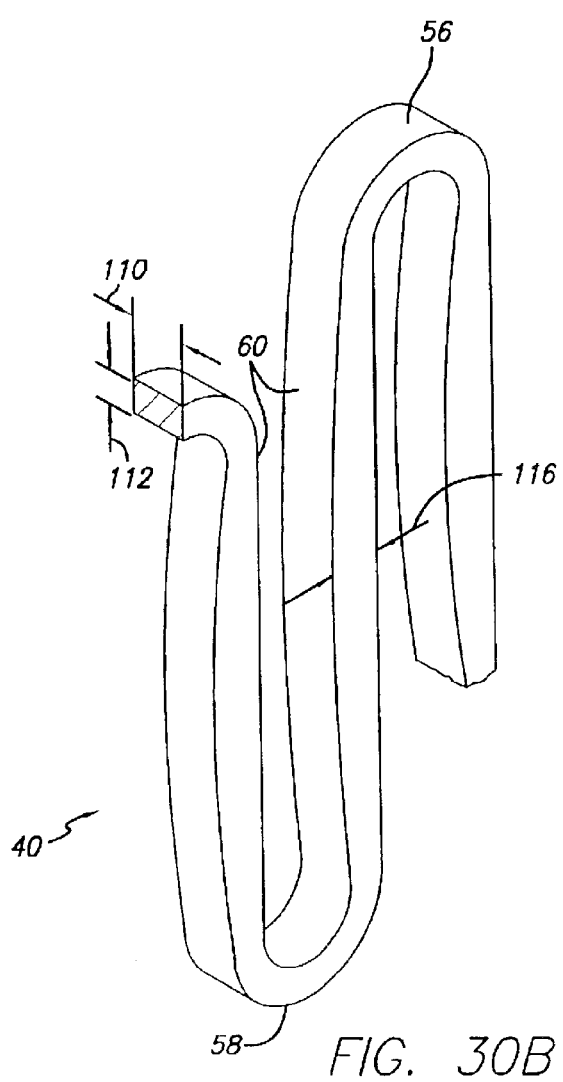
FIG. 30A
FIG. 30B

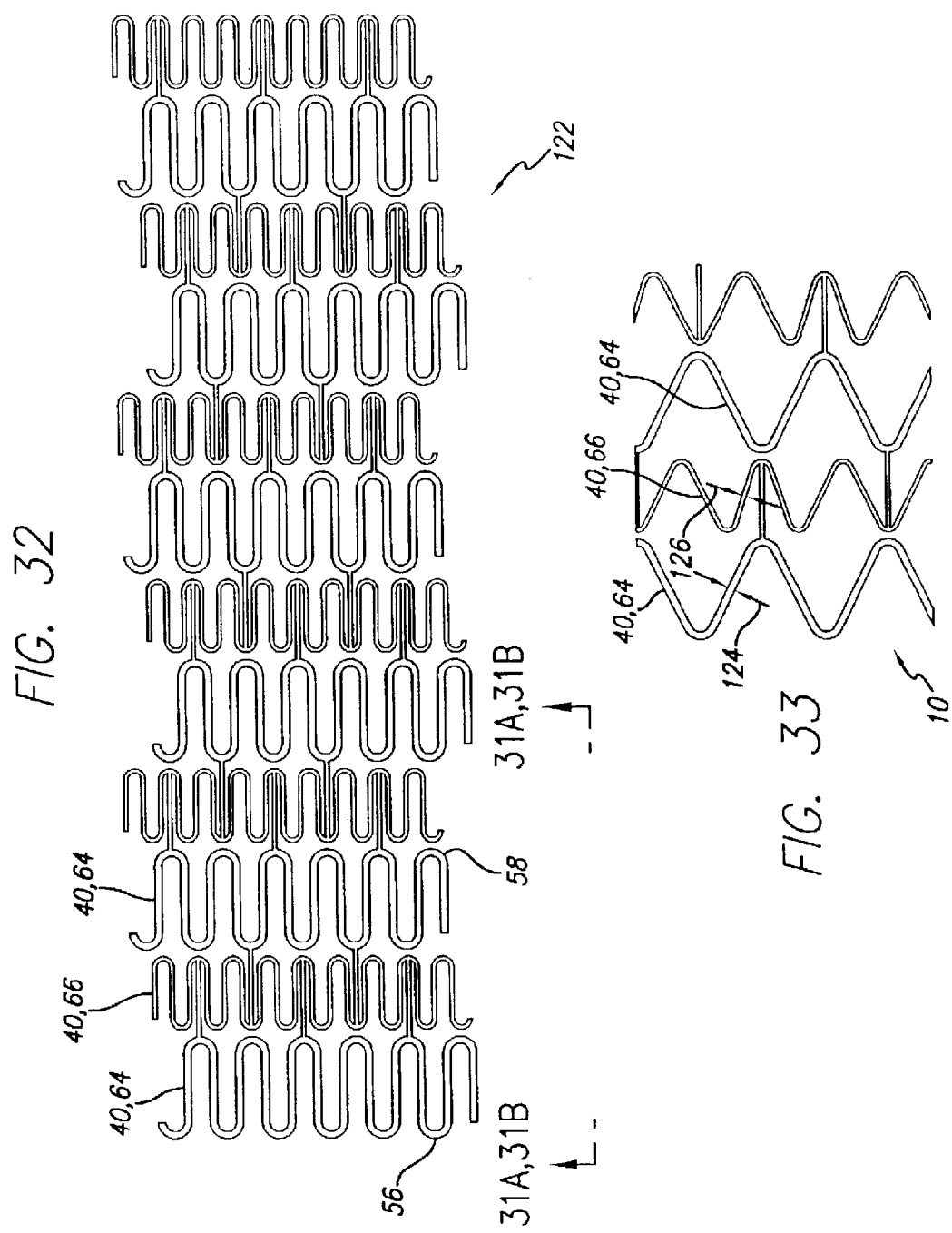

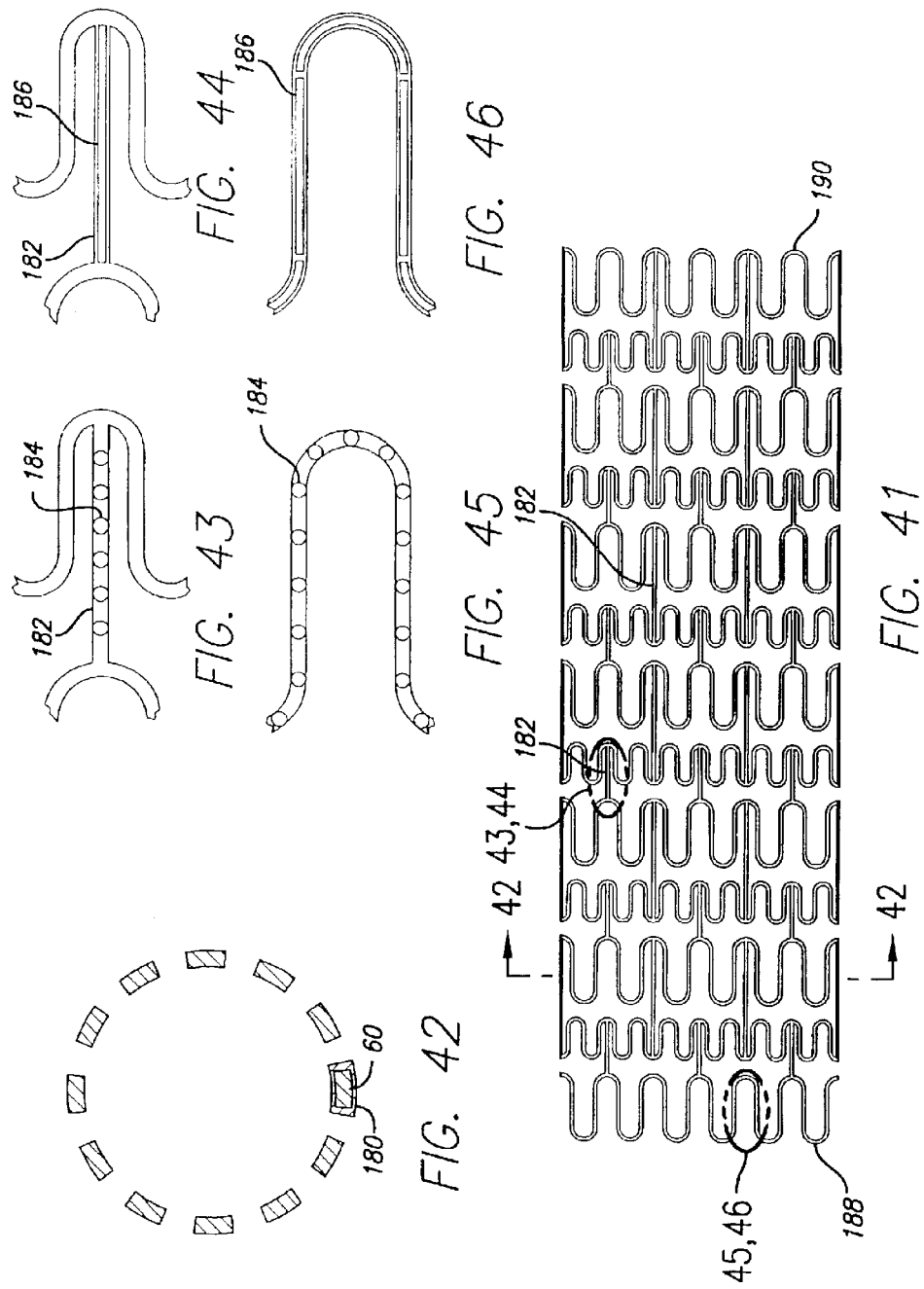

US 6,846,323 B2

INTRAVASCULAR STENT

BACKGROUND OF THE INVENTION

This invention relates to vascular repair devices, and in particular to intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis. Stents also can be used to provide primary compression to a stenosis in cases in which no initial PTCA or PTA procedure is performed. While stents are most often used in the procedures mentioned above, they also can be implanted on another body lumen such as the carotid arteries, peripheral vessels, urethra, esophagus and bile duct.

In typical PTCA procedures, a guiding catheter or sheath is percutaneously introduced into the cardiovascular system of a patient through the femoral arteries and advanced through the vasculature until the distal end of the guiding catheter is in the aorta. A guidewire and a dilatation catheter having a balloon on the distal end are introduced through the guiding catheter with the dilatation catheter sliding over the guidewire. The guidewire is first advanced out of the guiding catheter into the patient's vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressure to displace the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. Stents are generally cylindrically shaped devices which function to hold open and sometimes expand a segment of a blood vessel or other arterial lumen, such as a coronary artery. Stents are usually delivered in a radially compressed condition to the target location and then are deployed into an expanded condition to support the vessel and help maintain it in an open position. The stent is usually crimped tightly onto a delivery catheter and transported in its delivery diameter through the patient's vasculature. The stent is expandable upon application of a controlled force, often through the inflation of the balloon portion of the delivery catheter, which expands the compressed stent to a larger diameter to be left in place within the artery at the target location. The stent also may be of the self-expanding type formed from, for example, shape memory metals or super-elastic nickel-titanium (NiTi) alloys, which will automatically expand from a compressed state when the stent is advanced out of the distal end of the delivery catheter into the body lumen.

The above-described, non-surgical interventional procedures, when successful, avoid the necessity for major surgical operations. Some stents are formed of cylindrical rings which alternate in length between adjacent rings. The variation in cylindrical ring length affects the ability of some of these stents to conform to the natural curvature of a body lumen, such as a curve in a blood vessel. Stent conformability is a function of the sectional rigidity (the resistance to bending of the sectional elements) of a stent design, such as the rigidity of individual cylindrical rings making up the stent. The strut pattern of each of the cylindrical rings includes an undulating pattern of U-shaped portions with the curved portions of the U-shapes being positioned at the first, proximal and second, distal ends of the struts. The U-shapes at the first, proximal end of the cylindrical rings are referred to as peaks while the U-shapes at the second, distal end of the cylindrical rings are referred to as valleys. The peaks and valleys have struts extending therebetween. The rigidity of a cylindrical ring is determined by its geometric features, such as peak/valley radii and strut length. In general, stents with cylindrical rings having longer strut lengths have higher rigidity. Stents with low sectional rigidity generally conform to the body lumens better than stents with high sectional rigidity.

Another source of variation in sectional rigidity is the manner in which connecting elements, such as links, connect the cylindrical rings together. Link patterns which repeat themselves over a certain number of cylindrical rings can often be identified. Some stents have link patterns which repeat themselves over long intervals, thus leading to lower conformability.

Another concern on some stents is that peaks on one cylindrical ring point directly at valleys on an adjacent cylindrical ring in such manner that as the stent traverses and/or is deployed in a curved body lumen, the peaks and valleys on the inside portion of the curve tend to overlap, commonly known as "train wrecking", while the peaks and valleys on the outside portion of the curve tend to flare out, commonly known as "fish scaling". The overlap can cause an increase in the biological response to the implanted stent. The overlap may also cause the stent to catch on the balloon. Flaring, on the other hand, is a known contributor to plaque prolapse.

What has been needed is a stent having a reduced amount of variation in the length of the cylindrical rings and shorter intervals for the link patterns to improve conformability of the stent. What has also been needed is a stent that eliminates unsupported peaks and valleys pointing directly at each other or that increase the distance between unsupported peaks and valleys which point directly at each other. The present invention satisfies these needs.

SUMMARY OF THE INVENTION

The present invention is directed to an intravascular stent with reduced variation in the length of the cylindrical rings and having shorter intervals for the link patterns, thereby improving conformability of the stent. The invention is also directed to a stent having no unsupported peaks and valleys pointing directly at each other. The invention is further directed at a stent having an increased distance between unsupported peaks and valleys which point directly at each other.

The stent assembly embodying features of the invention can be readily delivered to the desired body lumen, such as a coronary artery (peripheral vessels, bile ducts, etc.), by mounting the stent assembly onto an expandable member of a delivery catheter, for example a balloon, and advancing the catheter and stent assembly through the body lumen to the target site. Generally, the stent is crimped onto the balloon portion of the catheter so that the stent assembly does not move longitudinally relative to the balloon portion of the catheter during delivery through the arteries, and during expansion of the stent at the target site. The stent is relatively flexible along its longitudinal axis to facilitate delivery through tortuous body lumens, yet is stiff and stable enough radially in an expanded condition to maintain the patency of a body lumen, such as an artery, when implanted therein.

In one embodiment, the stent includes cylindrical rings. Each cylindrical ring includes a strut pattern, a first end (e.g., proximal end) and a second end (e.g., distal end), with the first, proximal end and the second, distal end defining a ring length. The cylindrical rings are aligned along a common longitudinal axis forming the stent and radially expandable from a first, delivery diameter to a second, implanted diameter. The stent also includes at least one link coupling each pair of adjacent cylindrical rings. The strut pattern of each cylindrical ring includes an undulating pattern of U-shaped portions with the curved portions of the U-shapes being positioned at the first, proximal and second, distal ends of the struts. The U-shapes at the first, proximal end of the cylindrical rings are referred to as peaks while the U-shapes at the second, distal end of the cylindrical rings are referred to as valleys.

Adjacent cylindrical rings alternate between a first, longer ring length and a second, shorter ring length. The cylindrical rings of the first, longer ring length include fewer peaks and valleys than the cylindrical rings of the second, shorter ring length. The cylindrical rings of the first, longer ring length are positioned in phase with each other. The cylindrical rings of the second, shorter ring length are also positioned in phase with each other. At least one valley on the cylindrical rings of the first, longer ring length is coupled to a circumferentially aligned (aligned along a line on the circumference of the stent that is parallel to the longitudinal axis of the stent) valley on the distally adjacent cylindrical ring of the second, shorter ring length by a link.

In one aspect of the invention, at least one peak on each of the cylindrical rings of the second, shorter ring length may be coupled to a circumferentially aligned peak or valley on the distally adjacent cylindrical ring of the first, longer ring length by a link. Alternatively, at least one valley on each of the cylindrical rings of the second, shorter ring length may be coupled to a circumferentially aligned peak or valley on the distally adjacent cylindrical ring of the first, longer ring length by a link. At least one valley on at least one cylindrical ring of the second, shorter ring length may be coupled to a circumferentially offset peak on the distally adjacent cylindrical ring of the first, longer ring length by a link. The cylindrical rings of the second, shorter ring length may each include peaks at a first, proximal position and at least one peak at a second, more distal position along the longitudinal axis of the stent with the at least one peak at the second, more distal position being circumferentially aligned with valleys on the proximally adjacent cylindrical ring of the first, longer ring length. Similarly, the cylindrical rings of the second, shorter ring length may each include at least one valley at a first, proximal position and valleys at a second, more distal position along the longitudinal axis of the stent with the at least one valley at the first, proximal position being circumferentially aligned with peaks on the distally adjacent cylindrical ring of the first, longer ring length. In one embodiment, an undulating link couples at least one valley at the first, proximal position on at least one of the cylindrical rings of the second, shorter length to the circumferentially aligned peak at the second, more distal position on the distally adjacent cylindrical ring of the first, longer length. At least one of the links may include a straight configuration, an undulating configuration, or straight portions and at least one curved portion. The strut pattern of the cylindrical rings of the first, longer ring length may include a first width while the strut pattern of the cylindrical rings of the second, shorter ring length include a second width, such that the first strut pattern width is greater than the second strut pattern width and the ratio between the first and second strut pattern widths is within a range of about 1.10:1 to about 1.45:1. The ratio between the first, longer ring length and the second, shorter ring length may be within a range of about 1.1:1 to about 1.4:1. The ratio between the first, longer ring length and the second, shorter ring length may be within a range of about 1.6:1 to about 2.5:1. The first, longer ring length may be within a range of about 0.6–2.0 mm (0.024–0.079 inches) and the second, shorter ring length may be within a range of about 0.4–1.2 mm (0.016–0.047 inches). The radial thickness of the stent may vary along the length of the stent, such that the cylindrical rings of the first, longer ring length include a first radial thickness which is greater than a second radial thickness of the cylindrical rings of the second, shorter ring length. The circumferential distance between adjacent peaks and between adjacent valleys on the cylindrical rings may be variable about the circumference of the cylindrical rings, such that the peaks of each cylindrical ring are circumferentially offset from the valleys on the proximally adjacent cylindrical ring.

In another embodiment of the invention, the peaks of each cylindrical ring of the stent are circumferentially offset from the valleys on the proximally adjacent cylindrical ring. The circumferential distance between adjacent peaks on at least one of the cylindrical rings may be variable about the circumference of the cylindrical rings. Similarly, the circumferential distance between adjacent valleys on at least one of the cylindrical rings may be variable about the circumference of the cylindrical rings. At least one of the links may include at least one curved portion. At least one peak on at least one cylindrical ring may be coupled by a link to a circumferentially offset valley on the proximally adjacent cylindrical ring.

In another embodiment of the invention, the stent includes a plurality of cylindrical rings including a first, proximal ring, at least one central ring and a second, distal ring, with the central rings being positioned between the first, proximal ring and the second distal ring. The strut pattern of the first, proximal ring includes at least one group of adjacent valleys at a first, proximal position along the longitudinal axis of the stent and at least one group of adjacent valleys at a second, more distal position along the longitudinal axis of the stent. The strut pattern of the at least one central ring includes at least one group of adjacent peaks at a first, proximal position, at least one group of adjacent peaks at a second, more distal position, at least one group of adjacent valleys at a first, proximal position and at least one group of adjacent valleys at a second, more distal position along the longitudinal axis of the stent. The strut pattern of the second, distal ring includes at least one group of adjacent peaks at a first, proximal position and at least one group of adjacent peaks at a second, more distal position along the longitudinal axis of the stent. The valleys of the at least one group of adjacent valleys at the first, proximal position and the valleys of the at least one group of adjacent valleys at the second, more distal position of the first, proximal ring are circumferentially aligned with the peaks of the at least one group of adjacent peaks at the first, proximal position and the peaks of the at least one group of adjacent peaks at the second, more distal position of the distally adjacent central ring, respectively. The valleys of the at least one group of adjacent valleys at the first, proximal position and the valleys of the at least one group of adjacent valleys at the second, more distal position of the at least one central ring are circumferentially aligned with the peaks of the at least one group of adjacent peaks at the first, proximal position and the peaks of the at least one group of adjacent peaks at the second, more distal position of the distally adjacent cylindrical ring, respectively.

In one aspect of the invention, the circumferential distance between adjacent valleys at the second, more distal position of the cylindrical rings may be greater than the circumferential distance between adjacent valleys at the first, proximal position of the cylindrical rings and the circumferential distance between adjacent peaks at the first, proximal position of the cylindrical rings may be greater than the circumferential distance between adjacent peaks at the second, more distal position of the cylindrical rings. The number of valleys in the at least one group of adjacent valleys at the first, proximal position may be greater than the number of valleys in the at least one group of adjacent valleys at the second, more distal position, while the number of peaks in the at least one group of adjacent peaks at the second, more distal position may be greater than the number of peaks in the at least one group of adjacent peaks at the first, proximal position. The arc length of the at least one group of adjacent valleys at the first, proximal position may be substantially the same as the arc length of the at least one group of adjacent valleys at the second, more distal position while the arc length of the at least one group of adjacent peaks at the first, proximal position may be substantially the same as the arc length of the at least one group of adjacent peaks at the second, more distal position. The strut pattern of the first, proximal ring may include at least one group of adjacent peaks at a first, proximal position and at least one group of adjacent peaks at a second, more distal position along the longitudinal axis of the stent, with struts extending therebetween. Similarly, the strut pattern of the second, distal ring may include at least one group of adjacent valleys at a first, proximal position and at least one group of adjacent valleys at a second, more distal position along the longitudinal axis of the stent. At least one of the links may include at least one curved portion and/or a straight configuration.

In another embodiment, the stent includes adjacent cylindrical rings alternating between a first, longer ring length and a second, shorter ring length, with the cylindrical rings of the first, longer ring length having fewer peaks and valleys than the cylindrical rings of the second, shorter ring length. The radial thickness of the stent is variable along the length of the stent. The cylindrical rings of the first, longer ring length are out-of-phase with each other. The cylindrical rings of the second, shorter ring length each include peaks at a first, proximal position and at least one peak at a second, more distal position along the longitudinal axis of the stent. The at least one peak at the second, more distal position of each of the cylindrical rings of the second, shorter ring length are circumferentially aligned with valleys on the proximally adjacent cylindrical ring of the first, longer ring length. The cylindrical rings of the second, shorter ring length each include at least one valley at a first, proximal position and valleys at a second, more distal position along the longitudinal axis of the stent. The at least one valley at the first, proximal position of each of the cylindrical rings of the second, shorter ring length is circumferentially aligned with peaks on the distally adjacent cylindrical ring of the first, longer ring length. At least one valley on the cylindrical rings of the first, longer ring length is coupled to a circumferentially aligned valley on the distally adjacent cylindrical ring of the second, shorter ring length by a link.

Each of the embodiments of the invention can be readily delivered to the desired luminal location by mounting them on an expandable member of a delivery catheter, for example a balloon, and passing the catheter-stent assembly through the body lumen to the implantation site. A variety of means for securing the stents to the expandable member on the catheter for delivery to the desired location are available. It is presently preferred to crimp the stent onto the unexpanded balloon. Other means to secure the stent to the balloon include providing ridges or collars on the inflatable member to restrain lateral movement, using bioabsorbable temporary adhesives, or a retractable sheath to cover the stent during delivery through a body lumen.

In one embodiment, structures for the expandable cylindrical rings which form the stents of the present invention generally have circumferential undulations containing alternating peaks and valleys. The peaks and valleys are formed in generally U-, Y- and W shaped and patterns alternately aligned along the longitudinal axis.

While the cylindrical rings and links incorporated into the stent are generally not separate structures, they have been conveniently referred to as rings and links for ease of identification. Further, the cylindrical rings can be thought of as comprising a series of U-, Y- and W-shaped structures in a repeating pattern. While the cylindrical rings are not divided up or segmented into U's, Y's and W's, the pattern of cylindrical rings resembles such configuration. The U's, Y's and W's promote flexibility in the stent primarily by flexing and may tip radially outwardly as the stent is delivered through a tortuous vessel.

The links which interconnect adjacent cylindrical rings can have cross-sections similar to the cross-sections of the undulating components of the cylindrical rings. The links may be formed in a unitary structure with the expandable cylindrical rings, or they may be formed independently and mechanically secured between the expandable cylindrical rings. The links may be formed substantially linearly or with a plurality of undulations.

Preferably, the number, shape and location of the links can be varied in order to develop the desired coverage area and longitudinal flexibility. These properties are important to minimize alteration of the natural physiology of the body lumen into which the stent is implanted and to maintain the compliance of the body lumen which is internally supported by the stent. Generally, the greater the longitudinal flexibility of the stents, the easier and the more safely they can be delivered to the implantation site, especially where the implantation site is on a curved section of a body lumen, such as a coronary artery or a peripheral blood vessel, and especially saphenous veins and larger vessels.

The stent may be formed from a tube by laser cutting the pattern of cylindrical rings and links in the tube, by individually forming wire rings and laser welding them together, and by laser cutting a flat metal sheet in the pattern of the cylindrical rings and links and then rolling the pattern into the shape of the tubular stent and providing a longitudinal weld to form the stent.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, of a stent embodying features of the invention and which is mounted on a rapid-exchange delivery catheter and positioned within an artery.

FIG. 2 is an elevational view, partially in section, similar to that shown in FIG. 1 except that the stent is expanded within the artery, so that the stent embeds within the arterial wall.

FIG. 3 is an elevational view, partially in section, showing the expanded stent implanted within the artery after withdrawal of the rapid-exchange delivery catheter.

FIG. 4 is a plan view of a flattened stent of the invention which illustrates the pattern of the stent shown in FIGS. 1–3.

FIG. 5 is an enlarged sectional view of FIG. 4 depicting an U-shaped portion of the cylindrical ring.

FIG. 6 is an enlarged sectional view of FIG. 4 depicting an Y-shaped portion of the cylindrical ring.

FIG. 7 is an enlarged sectional view of FIG. 4 depicting a W-shaped portion of the cylindrical ring.

FIG. 8A is a side view of a stent embodying features of the invention in an unexpanded state.

FIG. 8B is a perspective view of the stent of FIG. 8A depicting the cylindrical wall defined by each cylindrical ring.

FIG. 10 is an enlarged view depicting struts of the cylindrical rings in a straight configuration.

FIG. 11 is an enlarged view depicting struts of the cylindrical rings in a curved configuration.

FIG. 12 is an enlarged view depicting a straight link coupling a peak on one cylindrical ring to a circumferentially aligned peak on a distally adjacent cylindrical ring.

FIG. 13 is an enlarged view depicting a straight link coupling a peak on one cylindrical ring to a circumferentially aligned valley on a distally adjacent cylindrical ring.

FIG. 14 is an enlarged view depicting an undulating link coupling a valley on one cylindrical ring to a circumferentially aligned peak on a distally adjacent cylindrical ring.

FIG. 15 is an enlarged view depicting a straight link coupling a valley on one cylindrical ring to a circumferentially aligned valley on a distally adjacent cylindrical ring.

FIG. 18 is an enlarged view depicting a straight link coupling a valley on one cylindrical ring to a circumferentially offset peak on a distally adjacent cylindrical ring.

FIG. 19 is an enlarged view depicting a link having straight portions and at least one curved portion coupling a valley on one cylindrical ring to a circumferentially offset valley on a distally adjacent cylindrical ring.

FIG. 22 is an enlarged view depicting a straight link coupling a valley on one cylindrical ring to a circumferentially aligned valley on a distally adjacent cylindrical ring.

FIG. 23 is an enlarged view depicting an undulating link coupling a valley on one cylindrical ring to a circumferentially aligned peak on a distally adjacent cylindrical ring.

FIG. 24 is an enlarged view depicting undulating links having straight struts extending perpendicular to the longitudinal axis of the stent and coupling to opposing sides of the apices of a peak and valley of adjacent cylindrical rings.

FIG. 25 is an enlarged view depicting undulating links having straight struts extending at an angle to the longitudinal axis of the stent and coupling to opposing sides of the apices of a peak and valley of adjacent cylindrical rings.

FIG. 26 is an enlarged view depicting undulating links having curved struts.

FIG. 27 is a plan view of a flattened stent of the invention which illustrates the pattern of another embodiment of the stent.

FIG. 28 is an enlarged view depicting undulating links coupling to the same side of the apices of a peak and valley of adjacent cylindrical rings.

FIG. 29 is an enlarged view depicting undulating links coupling to the apices of a peak and valley of adjacent cylindrical rings.

FIG. 30A is an enlarged view depicting a portion of a cylindrical ring having flexible portions and stable portions.

FIG. 30B is an enlarged view depicting a portion of a cylindrical ring having flexible portions and stable portions.

FIG. 31A is a partial side view of the stent of FIG. 4 depicting variable radial thickness along the length of the stent.

FIG. 31B is a partial side view of the stent of FIG. 4 depicting variable radial thickness along the length of the stent.

FIG. 32 is a plan view of a flattened stent of the invention which illustrates the pattern of another embodiment of the stent.

FIG. 33 is a partial plan view of a flattened stent of the invention depicting variable thickness between adjacent cylindrical rings.

FIG. 41 is a plan view of a flattened stent having a drug coating on selected portions.

FIG. 42 is a cross-sectional view taken along lines 42—42 depicting the drug coating on a portion of the stent.

FIG. 43 is an enlarged sectional view of FIG. 41 depicting a link of the stent with micro depots distributed along the link.

FIG. 44 is an enlarged sectional view of FIG. 41 depicting a link of the stent with micro channels distributed along the link.

FIG. 45 is an enlarged sectional view of FIG. 41 depicting a cylindrical ring of the stent with micro depots distributed along the cylindrical ring.

FIG. 46 is an enlarged sectional view of FIG. 41 depicting a cylindrical ring of the stent with micro channels distributed along the cylindrical ring.

DETAILED DESCRIPTION OF THE PREFERRED EMBODIMENTS

Figure 9A:
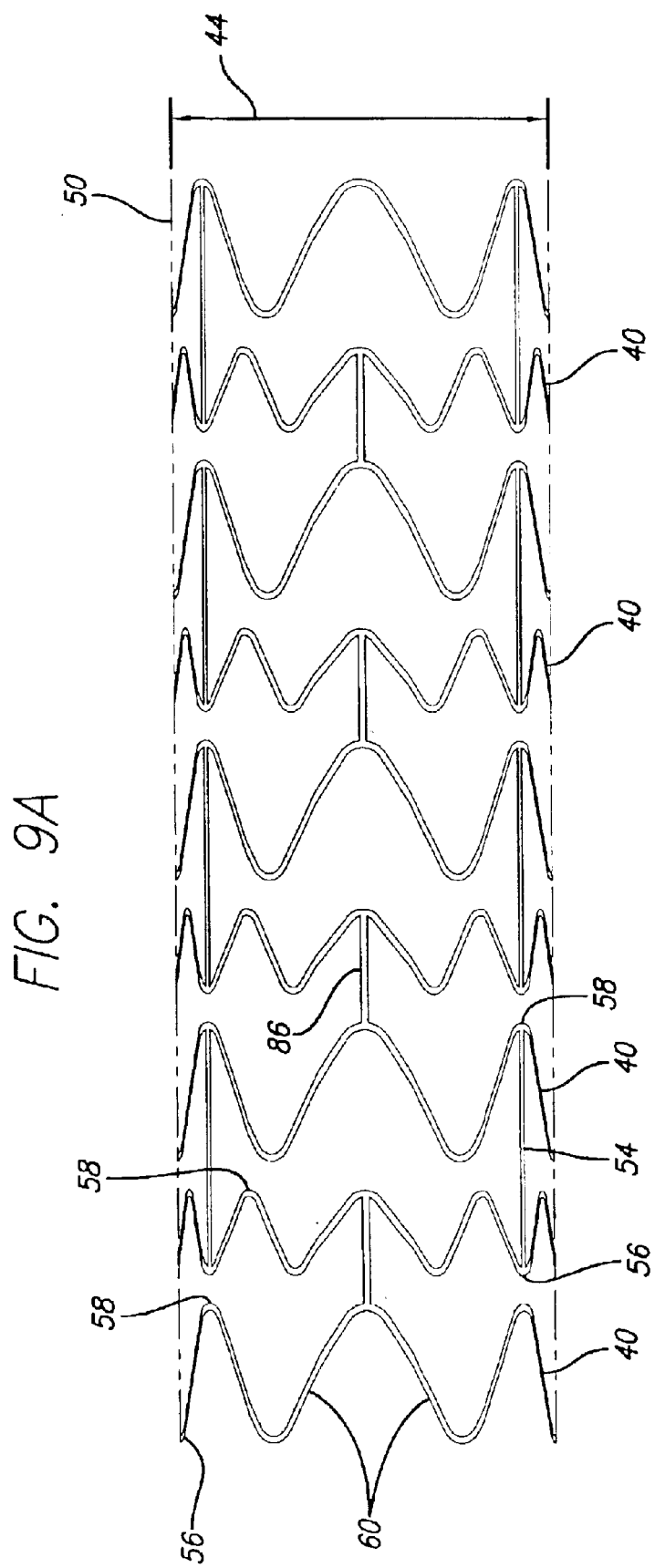
FIG. 9A is a side view of the stent of FIG. 8A in an expanded condition.
Figure 9B:
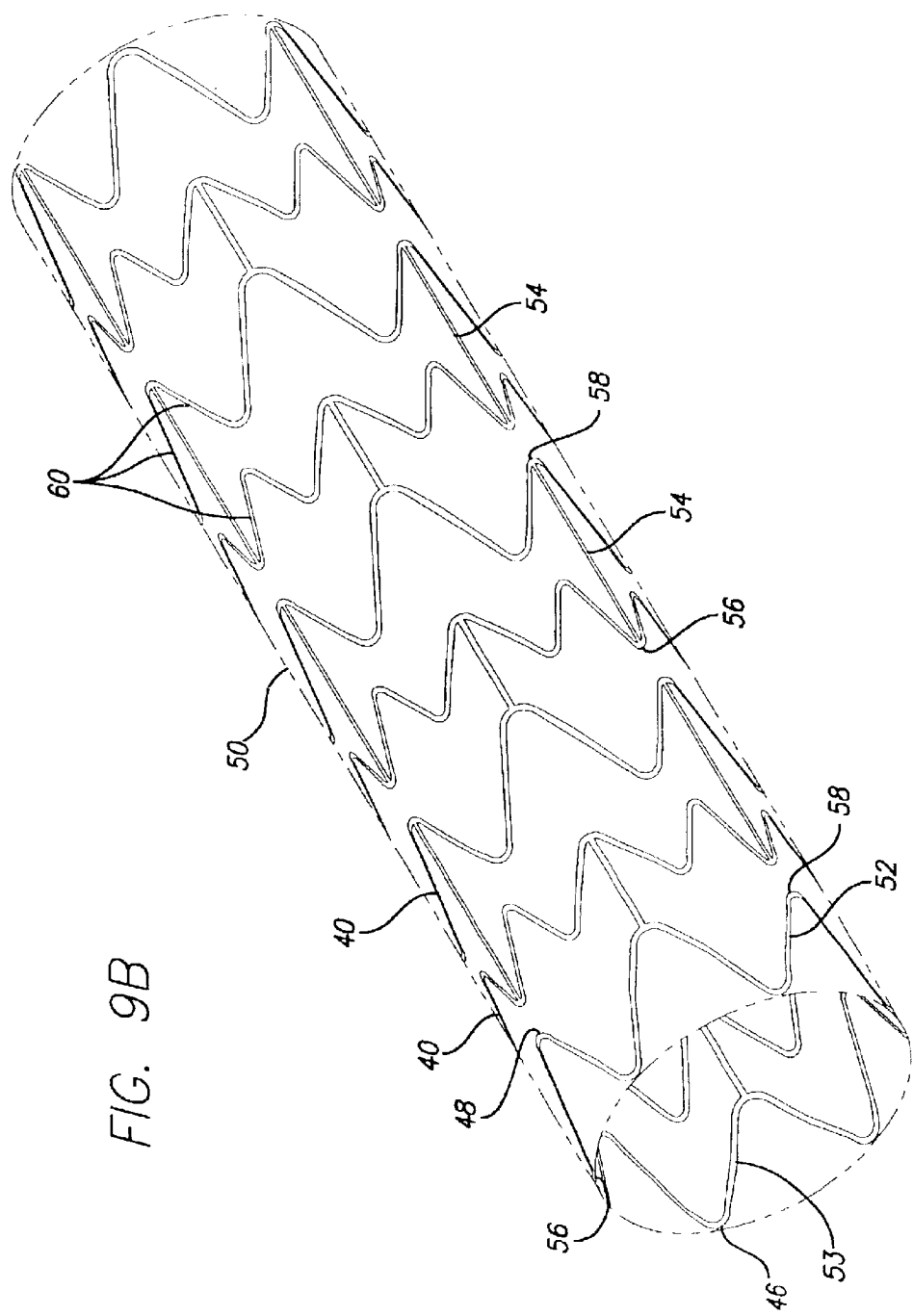
FIG. 9B is a perspective view of the stent of FIG. 8A in an expanded condition.

Before describing in detail an exemplary embodiment of a stent in accordance with the present invention, it is instructive to briefly describe a typical stent implantation procedure and the vascular conditions which are typically treated with stents. Turning to the drawings, FIG. 1 depicts stent 10 of the present invention mounted on a catheter assembly 12 which is used to deliver the stent and implant it in a body lumen, such as a coronary artery, peripheral artery, or other vessel or lumen within the body. The catheter assembly includes a catheter shaft 13 which has a first, proximal end 14 and a second, distal end 16. The catheter assembly is configured to advance through the patient's vascular system by advancing over a guide wire 18 by any of the well known methods of an over the wire system (not shown) or a well known rapid exchange catheter system, such as the one shown in FIG. 1.

The catheter assembly 12, as depicted in FIG. 1, is of the well known rapid exchange (RX) type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque 26 that has been previously treated by an angioplasty or other repair procedure. The stent 10 of the present invention is used to repair a diseased or damaged arterial wall which may include the plaque 26 as shown in FIG. 1. The stent of the invention is configured to repair the vessel having plaque.

In a typical procedure to implant the stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIG. 2, the balloon is fully inflated with the stent expanded and pressed against the vessel wall, and in FIG. 3, the implanted stent remains in the vessel after the balloon has been deflated and the catheter assembly and guide wire have been withdrawn from the patient.

Stent 10 serves to hold open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with smooth muscle cell growth which further minimizes blood flow interference. The undulating portion of the stent provides good tacking characteristics to prevent stent movement within the artery.

In keeping with the present invention, FIGS. 4–9B depict the stent 10 in various configurations. Turning to FIG. 4, stent 10 is shown in a flattened condition so that the pattern can be clearly viewed, even though the stent is never in this form unless it is formed from a flat sheet. The stent is typically formed from a tubular member; however, it can be formed from a flat sheet such as shown in FIG. 4 and rolled into a cylindrical configuration.

With respect to the structure of the cylindrical rings and links, virtually any pattern is acceptable. Typically, the rings are in the form generally of a zigzag pattern that can easily expand radially outwardly or compress radially inwardly. Thus, as described immediately below, an example of cylindrical rings 40 and links 54 are described, however, other patterns are envisioned that would perform equally well.

As shown in FIGS. 4–9B, stent 10 is made up of a plurality of cylindrical rings 40 having a strut pattern. The cylindrical rings extend circumferentially around the stent when it is in a tubular form (see FIGS. 8A, 8B, 9A and 9B) and are coaxially aligned along a common longitudinal axis which forms the stent. The stent is radially expandable, thus having a first, delivery diameter 42 as shown in FIG. 8A, and a second, implanted diameter 44 (expanded diameter) as shown in FIG. 9A. Each cylindrical ring 40 has a first end 46 (e.g., proximal end) and a second end 48 (e.g., distal end) with the distance between the first, proximal end and the second, distal end defining a ring length. Typically, since the stent is laser cut from a solid tube there are no discreet parts such as the described cylindrical rings. However, it is beneficial for identification and reference to various parts to refer to the cylindrical rings and the following parts of the stent.

Each cylindrical ring 40 defines a cylindrical plane 50 (FIG. 8B) which is a plane defined by the first, proximal and second, distal ends 46, 48 and the circumferential extent as the cylindrical ring travels around the cylinder. Each cylindrical ring includes a cylindrical outer wall surface 52 which defines the outermost surface of the stent, and a cylindrical inner wall surface 53 which defines the innermost surface of the stent. The cylindrical plane 50 follows the cylindrical outer wall surface. In keeping with the invention, the links 54 are positioned within the cylindrical plane 50. The links couple one cylindrical ring to an adjacent cylindrical ring.

Referring to FIGS. 4–9B, stent 10 can be described more particularly as having peaks 56 and valleys 58 with struts 60 positioned therebetween. Although the stent is not divided into separate elements, for ease of discussion references to peaks, valleys and struts is appropriate. The number of peaks and valleys, sometimes referred to as crowns, can vary in number for each ring depending upon the application. Thus, for example, if the stent is to be implanted in a coronary artery, a lesser number of peaks and valleys (or crowns) are required than if the stent is implanted in a peripheral artery, which has a larger diameter than a coronary artery. In one embodiment, the struts 60 of the cylindrical rings include a straight configuration 61 (FIGS. 4, 10), while in another embodiment (FIG. 11) the struts include a curved configuration 62.

Referring to FIGS. 5–7, the stent of the invention can be described as having cylindrical rings formed of U-shaped portions 30, Y-shaped portions 32, and W-shaped portions 34. Again, while the stent is generally laser cut from a tube and it typically has no discreet parts, for ease of identification the stent of the invention also can be referred to as having U-, Y-, and W-shaped portions. The U-shaped portions 30 have no supporting structure attached thereto. The Y-shaped portions 32, at their base, or apex, have the link 54 extending therefrom. The W-shaped portion 34 has the other end of the link attached at its base or curve portion. The length of the links can vary depending upon the desired amount of separation between adjacent cylindrical rings. In one embodiment, the link is contained within the W-shaped portion, which should be wide enough to accommodate the link when the stent is crimped so that no portion of the link and the W-portion overlap.

The undulations of the cylindrical rings 40 can have different degrees of curvature and angles of adjacent peaks 56 and valleys 58 to compensate for the expansive properties of the peaks and valleys. The cylindrical rings 40 of the stents are plastically deformed when expanded (except with NiTi alloys) so that the stents will remain in the expanded condition and therefore they must be sufficiently rigid when expanded to prevent the collapse thereof in use.

As can be seen in the embodiment of FIG. 4, the peaks 56, are positioned at the first, proximal end 46 of each cylindrical ring 40, and the valleys 58 are positioned at the second, distal end 48 of each cylindrical ring. Adjacent cylindrical rings 40 alternate between rings of a first ring length 64 and rings of a second ring length 66 with the first ring length being greater than the second ring length. A ratio between ring lengths for the cylindrical rings 40 of the first, longer ring length 64 and the second, shorter ring length 66 may be between about 1.1:1 and about 2.5:1. The ring length for the cylindrical rings of the first, longer ring length 64 may be between about 0.6–2.0 mm (0.024–0.079 inches), while the ring length for the cylindrical rings of the second, shorter ring length 66 may be between about 0.4–1.2 mm (0.016–0.047 inches). FIG. 4 depicts cylindrical rings of the first, longer ring length positioned at either end of the strut. However, the cylindrical rings 40 at the end of the stent may be of either the first 64 or second 66 ring length. Further, FIG. 4 depicts an embodiment where the ring length of the first, longer ring length and of the second, shorter ring length are uniform within each individual ring.

The cylindrical rings of the first, longer ring length 64 include fewer peaks 56 and valleys 58 than the cylindrical rings of the second, shorter ring length 66. For example, FIG. 4 depicts the cylindrical ring 40 of the first, longer ring length 64 having two peaks 56 for every three peaks on the cylindrical ring of the second, shorter ring length 66. However, other peak ratios between cylindrical rings of the first, longer and second, shorter lengths are within the scope of the invention. Such other peak ratios may include 2:4, 2:5, 3:4, 3:5 and 4:5. The alternating cylindrical rings of the first, longer ring length 64 are positioned in phase with each other, that is, the peaks of one ring of the first, longer ring length 64 are circumferentially aligned (i.e., aligned along lines on the circumference of the stent that are parallel to the longitudinal axis of the stent) with the peaks of the next ring of the first, longer ring length. Similarly, the alternating cylindrical rings of the second, shorter ring length 66 are positioned in phase with each other. Positioning the peaks, valleys, and links 54 in this manner, provides a stent having uniform expansion capabilities, high radial strength and sufficient wall coverage to support the vessel.

Figure 16:
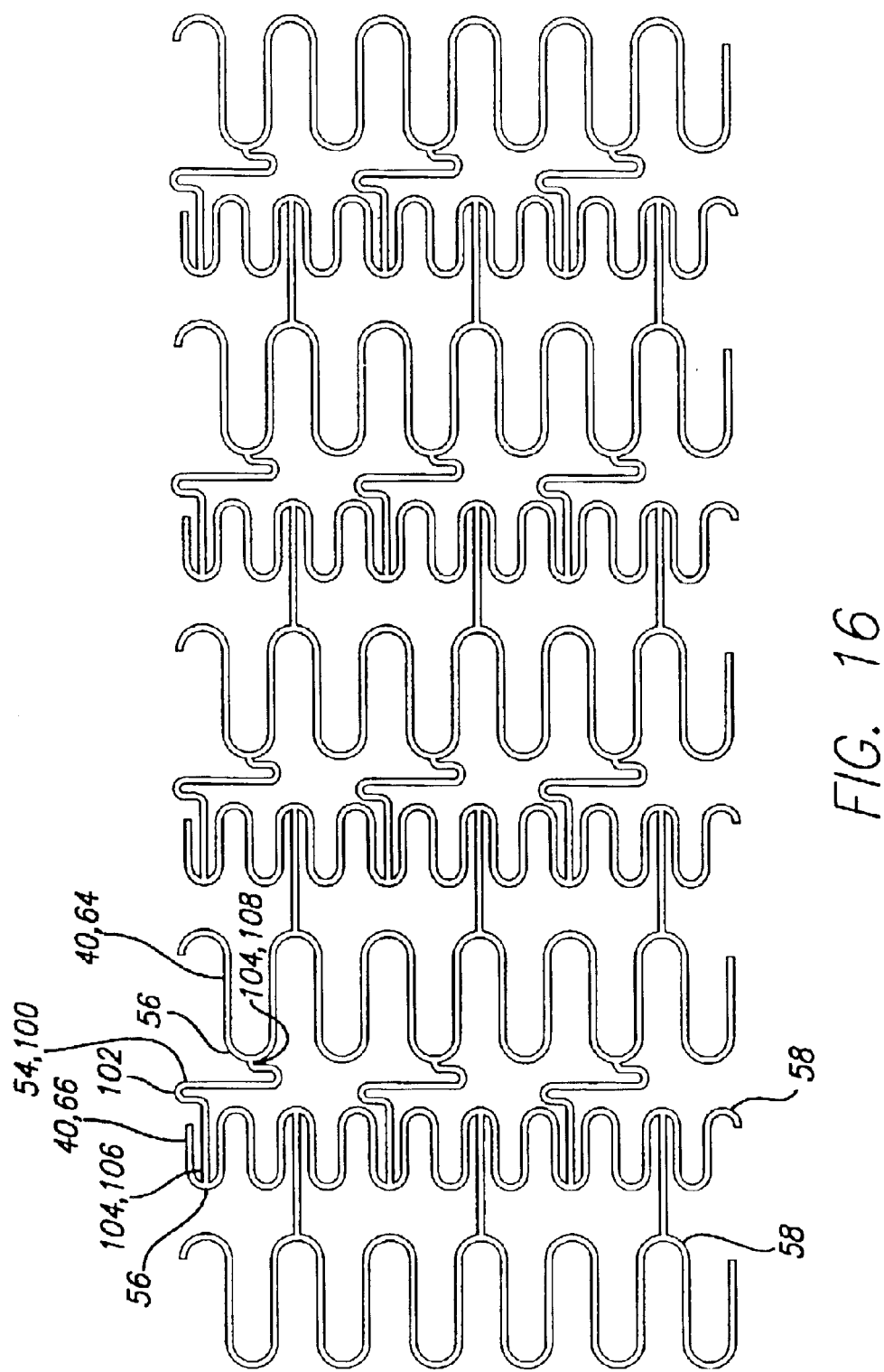
FIG. 16 is an enlarged view depicting a link having straight portions and at least one curved portion coupling a peak on one cylindrical ring to a circumferentially offset peak on a distally adjacent cylindrical ring.
Figure 17:
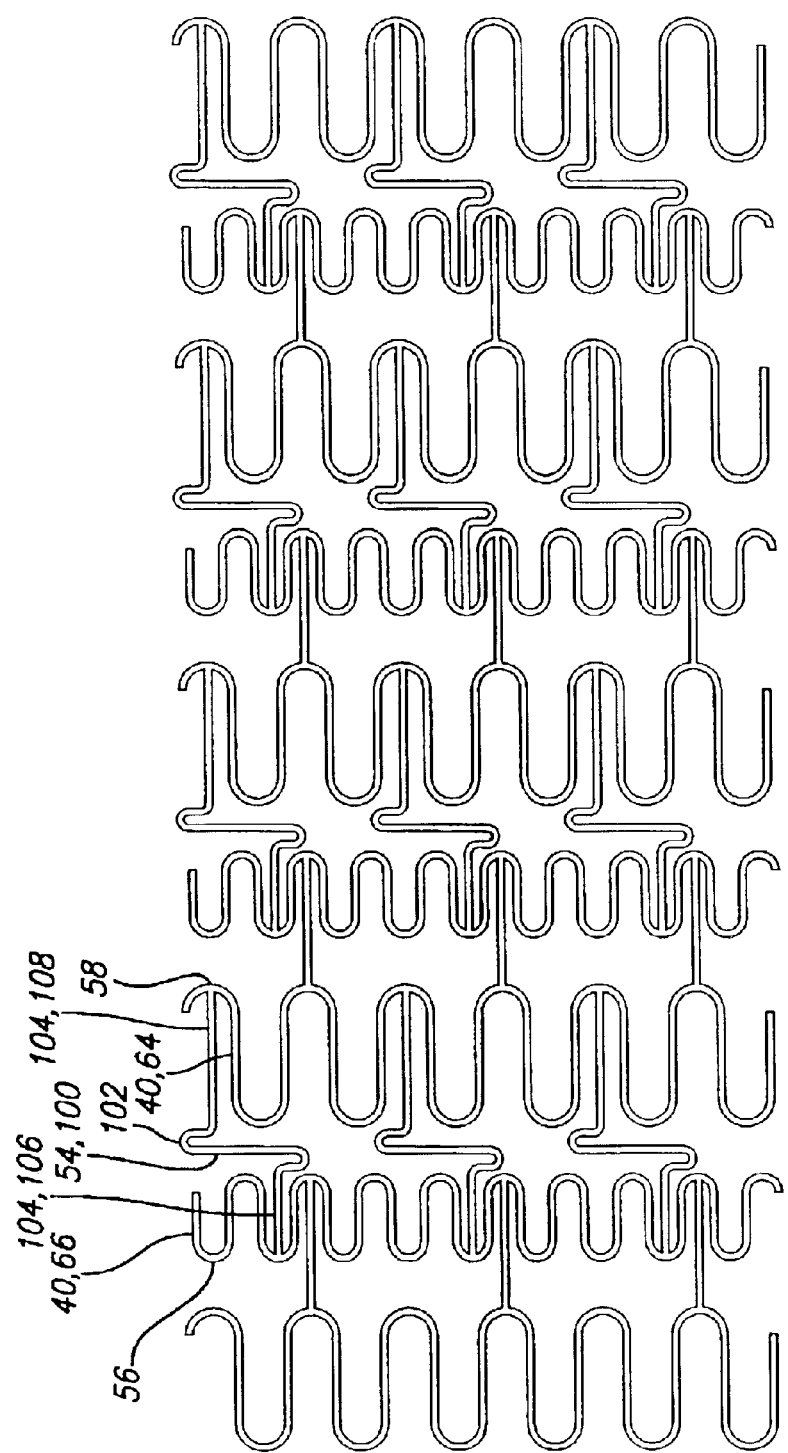
FIG. 17 is an enlarged view depicting a link having straight portions and at least one curved portion coupling a peak on one cylindrical ring to a circumferentially offset valley on a distally adjacent cylindrical ring.

With continued reference to FIG. 4, at least one valley 58 on the cylindrical rings 40 of the first, longer ring length 64 may be coupled to a circumferentially aligned valley 58 on the distally adjacent cylindrical ring of the second, shorter ring length 66 by a link 54 Links also couple the cylindrical rings of the second, shorter ring length 66 to the distally adjacent cylindrical rings of the first, longer ring length 64. For example, in one embodiment (see FIGS. 12 and 13) the cylindrical rings 40 of the second, shorter ring length 66 may include at least one peak 56 which is coupled to a circumferentially aligned peak 56 or valley 58 on the distally adjacent cylindrical ring of the first, longer ring length 64 by a link. Alternatively, in another embodiment (see FIGS. 14 and 15) the cylindrical rings 40 of the second, shorter ring length 66 may include at least one valley 58 which is coupled to a circumferentially aligned peak 56 or valley 58 on the distally adjacent cylindrical ring of the first, longer ring length 64 by a link 54. In a further embodiment (see FIGS. 16 and 17), links 54 may couple peaks 56 on the cylindrical rings 40 of the second, shorter ring length 66 to circumferentially offset peaks 56 or valleys 58 of the distally adjacent cylindrical ring of the first, longer ring length 64. Similarly, in an additional embodiment (see FIGS. 18 and 19), links 54 may couple valleys 58 on the cylindrical rings 40 of the second, shorter ring length 66 to circumferentially offset peaks 56 or valleys 58 of the distally adjacent cylindrical ring of the first, longer ring length 64.

Figure 20:
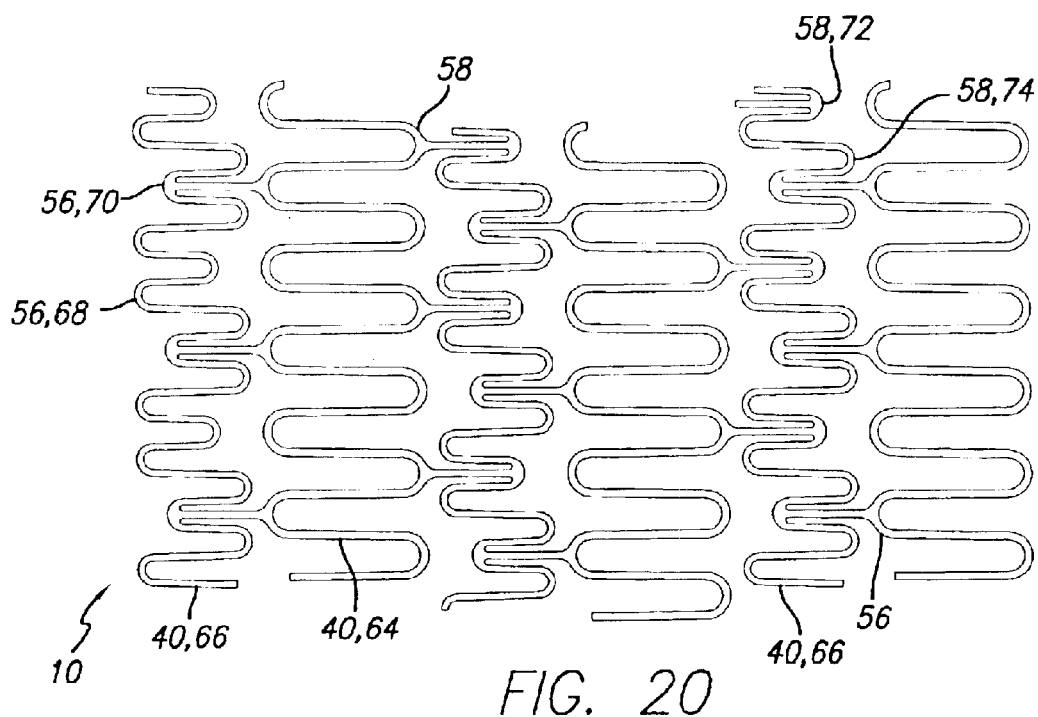
FIG. 20 is a plan view of a flattened stent of the invention which illustrates the pattern of another embodiment of the stent.

In one embodiment, as depicted in FIG. 20, the cylindrical rings 40 of the second, shorter ring length 66 each include peaks 56 at a first, proximal position 68 and at least one peak at a second, more distal position 70 along the longitudinal axis of the ring, as well as that of the stent 10. The at least one peak at the second, more distal position of each of the cylindrical rings of the second, shorter ring length is circumferentially aligned with, but not linked directly with, a valley on the proximally adjacent cylindrical ring of the first, longer ring length 64. Said peaks and valleys face each other and are near together in comparison to peaks and valleys which, although circumferentially aligned, face away from each other. Similarly, the cylindrical rings 40 of the second, shorter ring length 66 each include at least one valley 58 at a first, proximal position 72 and valleys at a second, more distal position 74 along the longitudinal axis of the ring and of the stent. The at least one valley 58 at the first, proximal position 72 of each of the cylindrical rings 40 of the second, shorter ring length 66 are circumferentially aligned with, but not linked directly with, peaks 56 on the distally adjacent cylindrical ring 40 of the first, longer ring length 64. In this manner, the distance between circumferentially aligned peaks 56 and valleys 58 which point directly at each other on adjacent cylindrical rings 40 is increased. The increased distance between the circumferentially aligned peaks and valleys reduces the likelihood of the peaks and valleys to overlap, or "train wreck", when the stent traverses or is deployed in a tortuous body lumen.

Figure 21:
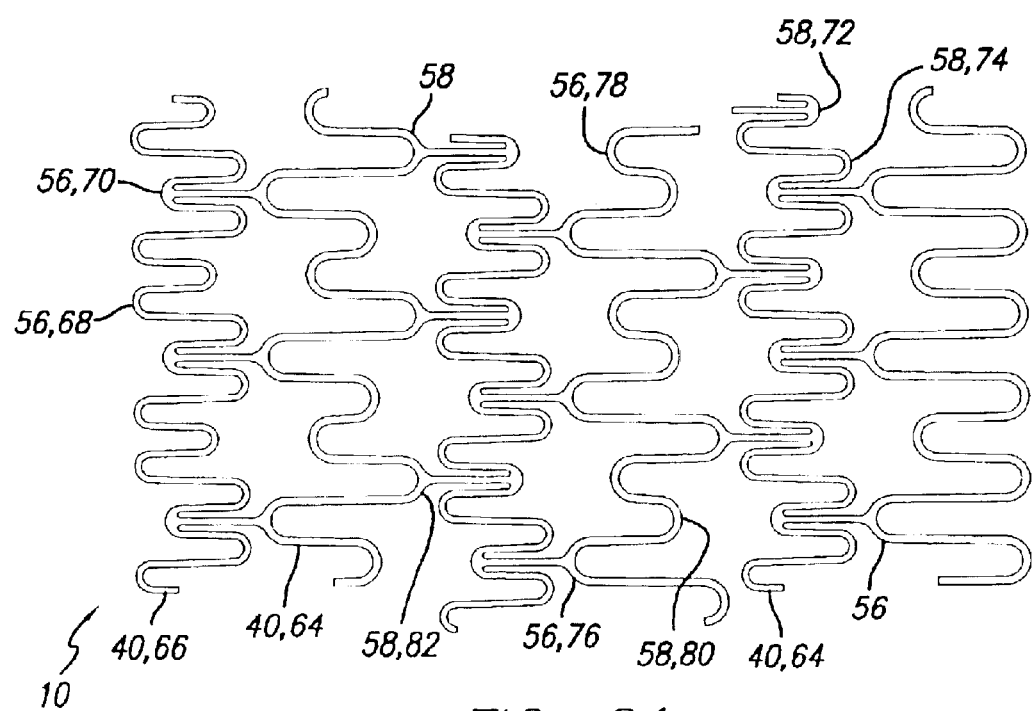
FIG. 21 is a plan view of a flattened stent of the invention which illustrates the pattern of another embodiment of the stent.

In another embodiment, depicted in FIG. 21, to further increase the distance between peaks 56 on one cylindrical ring 40 which are circumferentially aligned with, and point directly at valleys 58 on adjacent cylindrical rings 40, the cylindrical rings of the first, longer ring length 64 may also include peaks at a first, proximal position 76 and at a second, more distal position 78, and valleys at a first, proximal position 80 and at a second, more distal position 82. The peaks 56 at the second, more distal position 78 are circumferentially aligned with, but not linked directly with, the valleys 58 at the first, proximal position 72 on the proximally adjacent cylindrical ring 40 of the second ring length 66. Similarly, the valleys 58 at the first, proximal position 80 on the cylindrical rings 40 of the first, longer length 64 are circumferentially aligned with, but not linked directly with, the peaks 56 at the second, more distal position 78 on the distally adjacent cylindrical ring 40 of the second, shorter ring length 66. In this manner, the likelihood of the circumferentially aligned peaks and valleys to overlap is reduced even further than when only one of the adjacent cylindrical rings includes peaks and valleys at varying longitudinal positions along the length of the stent. Furthermore, as with the stent depicted in FIG. 20, the amount of flaring, or fish scaling, between the circumferentially aligned peaks 56 and valleys 58 is reduced because the length of the struts 60 extending from the peaks and valleys is reduced.

In one embodiment, the links 54 positioned between a cylindrical ring 40 of the first, longer ring length 64 and a distally adjacent cylindrical ring of the second, shorter ring length 66 may include a straight configuration 84 (FIGS. 4, 22) that is parallel to the longitudinal axis of the stent 10. The straight links 84 may provide rigidity to the stent and improve the crimping force onto the expandable member 22. The links 54 may also include an undulating configuration 86 to maximize flexibility of the stent. The undulating links connect one cylindrical ring 40 to an adjacent cylindrical ring. In one embodiment (FIG. 23), undulating links 86 may couple valleys 58, such as a valley at the first, proximal position 72, on a cylindrical ring 40 of the second, shorter length 66 to peaks 56, such as peaks at the second, more distal position 78, on a distally adjacent cylindrical ring of the first, longer length 64. The undulating links 86 provide overall longitudinal flexibility to the stent 10 due to their unique construction. The flexibility of undulating links derives in part from curved portions 88 with struts 90 extending therebetween. In one configuration (FIG. 24), the struts 90 are straight and extend substantially perpendicular to the longitudinal axis of the stent. With the struts being substantially perpendicular to the stent longitudinal axis, the undulating link acts like a hinge to provide flexibility. Thus, as the stent is being delivered through a tortuous vessel, such as a coronary artery, the curved portions 88 and straight struts 90 of the undulating links will permit the stent to flex in the longitudinal direction, which substantially enhances delivery of the stent to the target site. Undulating links 92 of an alternate embodiment (FIG. 25) include straight struts 94 positioned at an angle to the longitudinal axis of the stent to form longer straight portions thereby increasing the flexibility of the links by providing longer moment arms. The longer struts positioned at the angel also increase vessel wall coverage. In a further embodiment (FIG. 26), the links 96 may include curved struts 98. The number of curved portions and struts can be increased or decreased from that shown to achieve constructions of differing flexibility.

Referring to FIG. 27, the stent 10 may also include links 100 having the at least one curved portion 102 and straight portions 104. The straight portions 104 of the link 102 include a first, proximal arm 106 and a second, more distal arm 108 which extend substantially longitudinally and parallel to the longitudinal axis of the stent. The at least one curved portion is positioned between the first and second arms. The links 100 may couple adjacent cylindrical rings 40 with the first, proximal arm 106 of each link being coupled to a valley 58 on one ring 40 and the second, more distal arm 108 being coupled to a valley 58 on the distally adjacent cylindrical ring (FIG. 19). Alternatively, the links 100 may couple adjacent cylindrical rings 40 with the first, proximal arm 106 of each link being coupled to a peak 56 on one ring 40 and the second, more distal arm 108 being coupled either to a peak 56 (FIG. 16) or to a valley 58 (FIGS. 17 and 27) on the distally adjacent cylindrical ring. In one embodiment, the link 100 is configured such that the at least one curved portion 102 is positioned between the adjacent pair of rings (FIG. 27). In another embodiment, the at least one curved portion 102 may be positioned between struts 60 on one of the cylindrical rings to which the link is coupled (FIG. 27).

In one embodiment of the invention (FIG. 24), a proximal end of an undulating link 86 may be coupled to a valley 58 of one ring 40 at a position a distance from the apex of the valley. A distal end of the undulating link 86 may be coupled to a circumferentially aligned peak 56 of the distally adjacent ring at a position a distance from the apex of the peak. The proximal and distal ends of the undulating link 86 may be coupled to opposing sides of the apices of the peak and valley (FIG. 24). However, in another embodiment (FIG. 28) of the undulating link 86, the proximal and distal ends may be coupled to the same side of the apices of the peak and valley. In a further embodiment (FIG. 29), the proximal and distal ends of the undulating link 86 attach to the apices of the valley 58 of one ring 40 and the peak 56 of the distally adjacent ring 40 respectively. In this embodiment, the links include a first or proximal arm 87 which couples to the valley of one ring and a second or distal arm 89 which couples to the peak of the distally adjacent ring. The first and second arms extend substantially longitudinally and parallel to the longitudinal axis of the stent.

It may be desirable in some embodiments to increase the strength of some portions of the stent while maintaining flexibility of the stent. With reference to FIGS. 30A, 30B, one embodiment of the invention includes flexing portions and stable portions. The flexing portions maintain flexibility and the stable portions have increased strength. For instance, the flexing portions of the stent may include the peaks 56 and the valleys 58 of the cylindrical rings 40. Accordingly, the peaks and valleys may have a nominal radial thickness 110 and a nominal width 112 which maintains flexibility of the cylindrical rings at the peaks and valleys. The stable portions of the stent may include the struts 60 between the peaks and valleys. Hence, the struts between the peaks and valleys may include a greater-than-nominal radial thickness 114 (FIG. 30A) or width 116 (FIG. 30B), or both radial thickness and width, to increase the strength of the struts.

Although the example disclosed refers to particular portions of the stent having the varying radial thickness or width, the portions of the stent including the nominal radial thickness and the greater-than-nominal radial thickness may vary as desired to attain varying degrees of strength within the stent.

In another embodiment (FIGS. 31A and 31B), the radial thickness of the stent 10 may be variable along the length of the stent. For example, the cylindrical rings 40 of the first, longer ring length 64 may include a first radial thickness 118 which is greater than a second radial thickness 120 of the cylindrical rings of the second, shorter ring length 66. The smaller, second radial thickness 120 of the cylindrical rings of the second, shorter ring length 66 improves the flexibility of the stent. The first 118 and second 120 radial thicknesses may be constant (FIG. 31A) about the circumference of the stent or the thickness of the stent may taper (FIG. 31B) between the first 118 and second radial thickness about the circumference of the stent. Stents designs of other strut patterns may also incorporate varying thickness between cylindrical rings. For example, a stent 122 (FIG. 32) similar to the stent 10 of FIG. 4 may also include varying radial thickness. The stent 122 includes the cylindrical rings 40 of the first longer length 64 positioned out-of-phase, that is, with the peaks 56 of one ring of the first, longer ring length 64 being circumferentially aligned with the valleys 58 of the next ring of the first, longer ring length.

In alternative embodiments (not shown), the cylindrical rings of the second, shorter ring length 66 may include the first radial thickness 118 while the cylindrical rings 40 of the first, longer ring length 64 include the smaller, second radial thickness 120, or the stent thickness may vary about the circumference of the stent. The variation in stent radial thickness may be obtained through the use of a laser to remove material from the stent, or through other methods that are well known in the art.

In another embodiment (FIG. 33), the width of the strut patterns of the stent 10 may be variable along the length of the stent. For example, the strut pattern of the cylindrical rings 40 of the first, longer ring length 64 may include a first width 124 and the strut pattern of the cylindrical rings of the second, shorter ring length 66 may include a second width 126. The width of the strut pattern of the cylindrical rings 40 of the first, longer ring length 64 may be greater than the width of the strut pattern of the cylindrical rings of the second, shorter ring length 66. A ratio between the width of the strut pattern of the cylindrical rings 40 of the first, longer ring length 64 and the width of the strut pattern of the cylindrical rings of the second, shorter ring length 66 may be within a range of about 1.1:1 to about 2.0:1, but preferably within a range of about 1.10:1 to about 1.45:1.

The aforementioned features of the stent 10, and the varying embodiments thereof as depicted in FIGS. 10–33, may be incorporated into stents of the following embodiments. For the sake of clarity, structural elements in the following embodiments that correspond with those in FIGS. 1–33 use the same reference numbers.

Figure 34:
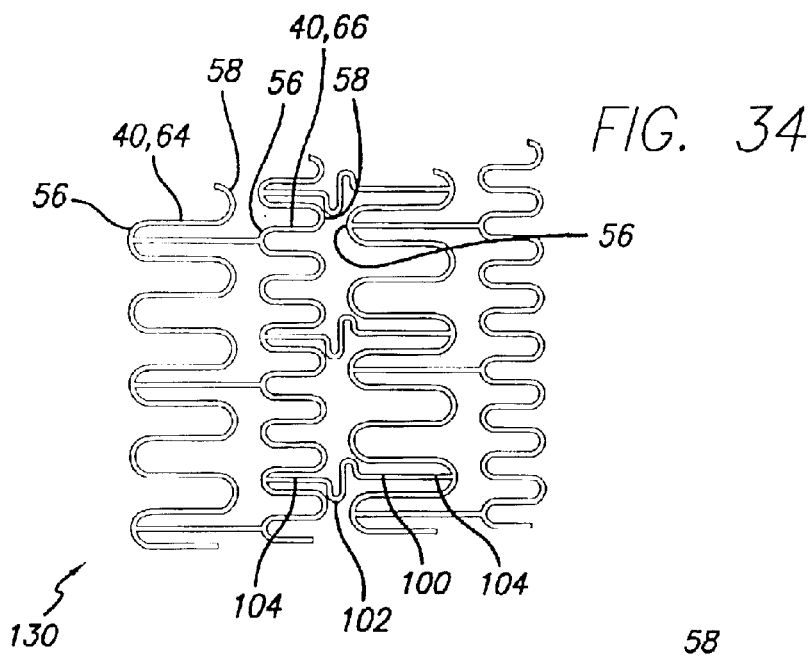
FIG. 34 is a plan view of a flattened stent of the invention which illustrates the pattern of another embodiment of the stent.
Figure 35:
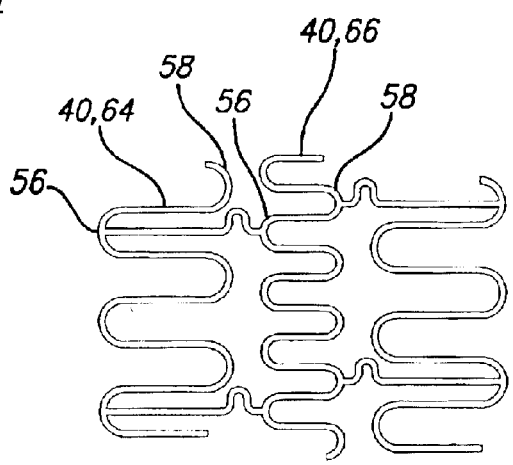
FIG. 35 is a plan view of a flattened stent of the invention which illustrates the pattern of another embodiment of the stent.
Figure 36:
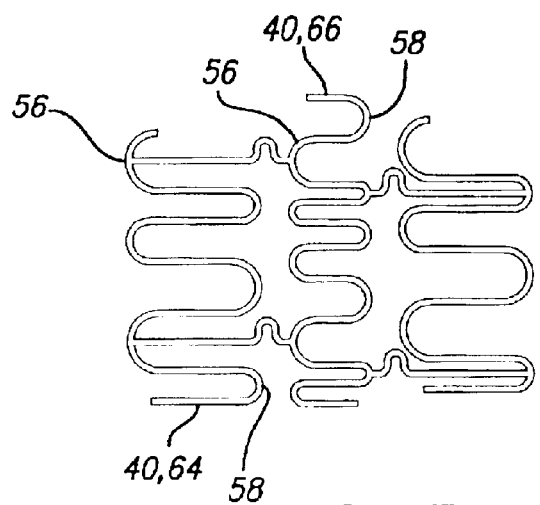
FIG. 36 is a plan view of a flattened stent of the invention which illustrates the pattern of another embodiment of the stent.

Referring to FIG. 34, another embodiment of the invention, which is similar to the embodiment depicted in FIG. 4, includes a stent 130 having the peaks 56 on each cylindrical ring 40 circumferentially offset from the valleys 58 on the proximally adjacent cylindrical ring. In this manner, the likelihood of peaks 56 and valleys 58 on adjacent cylindrical rings 40 overlapping, or "train wrecking", while the stent is traversing or being deployed in a tortuous body lumen is reduced because no peaks 56 on one ring are pointing directly at a valley 58 on the proximally adjacent cylindrical ring. One method to have the peaks 56 of one cylindrical ring 40 circumferentially offset from the valleys 58 of the proximally adjacent cylindrical ring is through the circumferential arrangement of the cylindrical rings (FIG. 34). The links 54 of this embodiment may include the links 100 having the at least one curved portion 102 and straight portions 104 to maintain flexibility within the stent. Another method (FIG. 35) for having the peaks 56 of one cylindrical ring 40 circumferentially offset from the valleys 58 of the proximally adjacent cylindrical ring is through the peak to valley ratio between the adjacent cylindrical rings. A further method (FIG. 36) to have the peaks 56 of one cylindrical ring 40 circumferentially offset from the valleys 58 of the proximally adjacent cylindrical ring is to include peaks 56 of varying radii within at least one cylindrical ring and/or valleys 58 of varying radii within at least one cylindrical ring. The varying radii of the peaks and valleys cause the distance between adjacent peaks and adjacent valleys to vary also. In this manner, the radii of the peaks and/or valleys can be controlled to ensure that no peaks on a cylindrical ring are circumferentially aligned with a valley on the proximally adjacent cylindrical ring.

Figure 37:
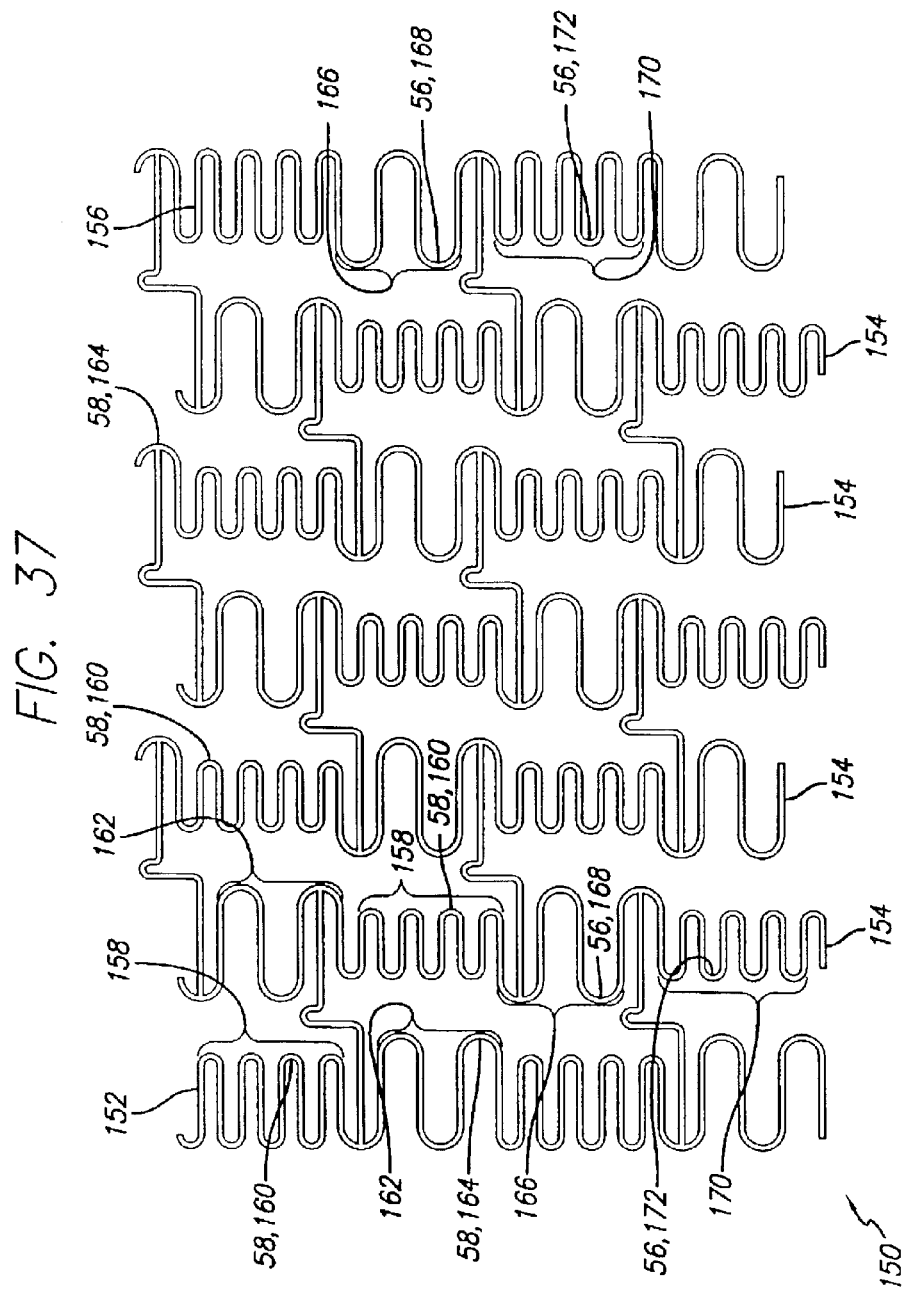
FIG. 37 is a plan view of a flattened stent of the invention which illustrates the pattern of another embodiment of the stent.

With reference to FIG. 37, a further embodiment of the invention is shown. In this embodiment, a stent 150 includes a first, proximal cylindrical ring 152, at least one central cylindrical ring 154 and a second, distal cylindrical ring 156, with the at least one central cylindrical ring being positioned between the first, proximal ring and the second, distal ring. The strut pattern of the first, proximal cylindrical ring 152 includes at least one group 158 of adjacent valleys 58 at a first, proximal position 160 along the longitudinal axis of the stent and at least one group 162 of adjacent valleys at a second, more distal position 164 along the longitudinal axis of the stent. The strut pattern of the second, distal cylindrical ring 156 includes at least one group 166 of adjacent peaks 56 at a first, proximal position 168 along the longitudinal axis of the stent and at least one group 170 of adjacent peaks at a second, more distal position 172 along the longitudinal axis of the stent. The strut pattern of the at least one central cylindrical ring 154 includes at least one group 158 of adjacent valleys 58 at a first, proximal position 160 along the longitudinal axis of the stent and at least one group 162 of adjacent valleys at a second, more distal position 164 along the longitudinal axis of the stent. The strut pattern of the at least one central cylindrical ring 154 also includes at least one group 166 of adjacent peaks 56 at a first, proximal position 168 along the longitudinal axis of the stent and at least one group 170 of adjacent peaks at a second, more distal position 172 along the longitudinal axis of the stent.

With continued reference to FIG. 37, the valleys 58 of the at least one group 158 of adjacent valleys at the first, proximal position 160 of the first, proximal cylindrical ring 152 may be circumferentially aligned with the peaks 56 of the at least one group 166 of adjacent peaks at the first, proximal position 168 of the distally adjacent central cylindrical ring 154. The valleys 58 of the at least one group 162 of adjacent valleys at the second, more distal position 164 of the first, proximal cylindrical ring 152 may be circumferentially aligned with the peaks 56 of the at least one group 170 of adjacent peaks at the second, more distal position 172 of the distally adjacent central cylindrical ring 154. The valleys 58 of the at least one group 158 of adjacent valleys at the first, proximal position 160 of the at least one central cylindrical ring are circumferentially aligned with the peaks 56 of the at least one group 166 of adjacent peaks at the first, proximal position 168 of the distally adjacent cylindrical ring 154, 156. The valleys 58 of the at least one group 162 of adjacent valleys at the second, more distal position 164 of the at least one central cylindrical ring 154 are circumferentially aligned with the peaks 56 of the at least one group 170 of adjacent peaks at the second, more distal position 172 of the distally adjacent cylindrical ring 154,156.

With further reference to FIG. 37, the circumferential distance between adjacent valleys 58 at the second, more distal position 164 of the first, proximal cylindrical ring 152 may be greater than the circumferential distance between adjacent valleys 58 at the first, proximal position 160 of the first, proximal cylindrical ring 152. The circumferential distance between adjacent peaks 56 at the first, proximal position 168 of the at least one central cylindrical ring 154 may be greater than the circumferential distance between adjacent peaks at the second, more distal position 172 of the at least one central cylindrical ring. Similarly, the circumferential distance between adjacent valleys 58 at the second, more distal position 164 of the at least one central cylindrical ring 154 may be greater than the circumferential distance between adjacent valleys at the first, proximal position 160 of the at least one central cylindrical ring. The circumferential distance between adjacent peaks 56 at the first, proximal position 168 of the second, distal cylindrical ring 156 may be greater than the circumferential distance between adjacent peaks at the second, more distal position 172 of the second, distal cylindrical ring. The number of valleys 58 in the at least one group 158 of adjacent valleys at the first, proximal position 160 may be greater than the number of valleys in the at least one group 162 of adjacent valleys at the second, more distal position 164. Similarly, the number of peaks 56 in the at least one group 170 of adjacent peaks at the second, more distal position 172 may be greater than the number of peaks in the at least one group 166 of adjacent peaks at the first, proximal position 168.

In any of the first, proximal 152 and central 154 cylindrical rings, the arc length of the at least one group 158 of adjacent valleys 58 at the first, proximal position 160 may be substantially the same as the arc length of the at least one group 162 of adjacent valleys at the second, more distal position 164. Similarly, in any of the central 154 and second, distal 156 cylindrical rings, the arc length of the at least one group 166 of adjacent peaks 56 at the first, proximal position 168 may be substantially the same as the arc length of the at least one group 170 of adjacent peaks at the second, more distal position 172. In one embodiment, the peaks 56 of the at least one group 166 of adjacent peaks at the first, proximal position 168 of the at least one central cylindrical ring 154 may be circumferentially aligned with the valleys 58 of the at least one group 162 of adjacent valleys at the second, more distal position 164 of the at least one central cylindrical ring. Similarly, the peaks 56 of the at least one group 170 of adjacent peaks at the second, more distal position 172 of the at least one central cylindrical ring 154 may be circumferentially aligned with the valleys 58 of the at least one group 158 of adjacent valleys at the first, proximal position 160 of the at least one central cylindrical ring. With adjacent cylindrical rings 40 circumferentially aligned in this manner, there is sufficient distance between groups of circumferentially aligned peaks and valleys on adjacent rings to reduce the likelihood of the peaks and valleys to overlap, or "train wreck", when the stent 150 is traversing or being deployed within a tortuous body lumen.

Figure 38:
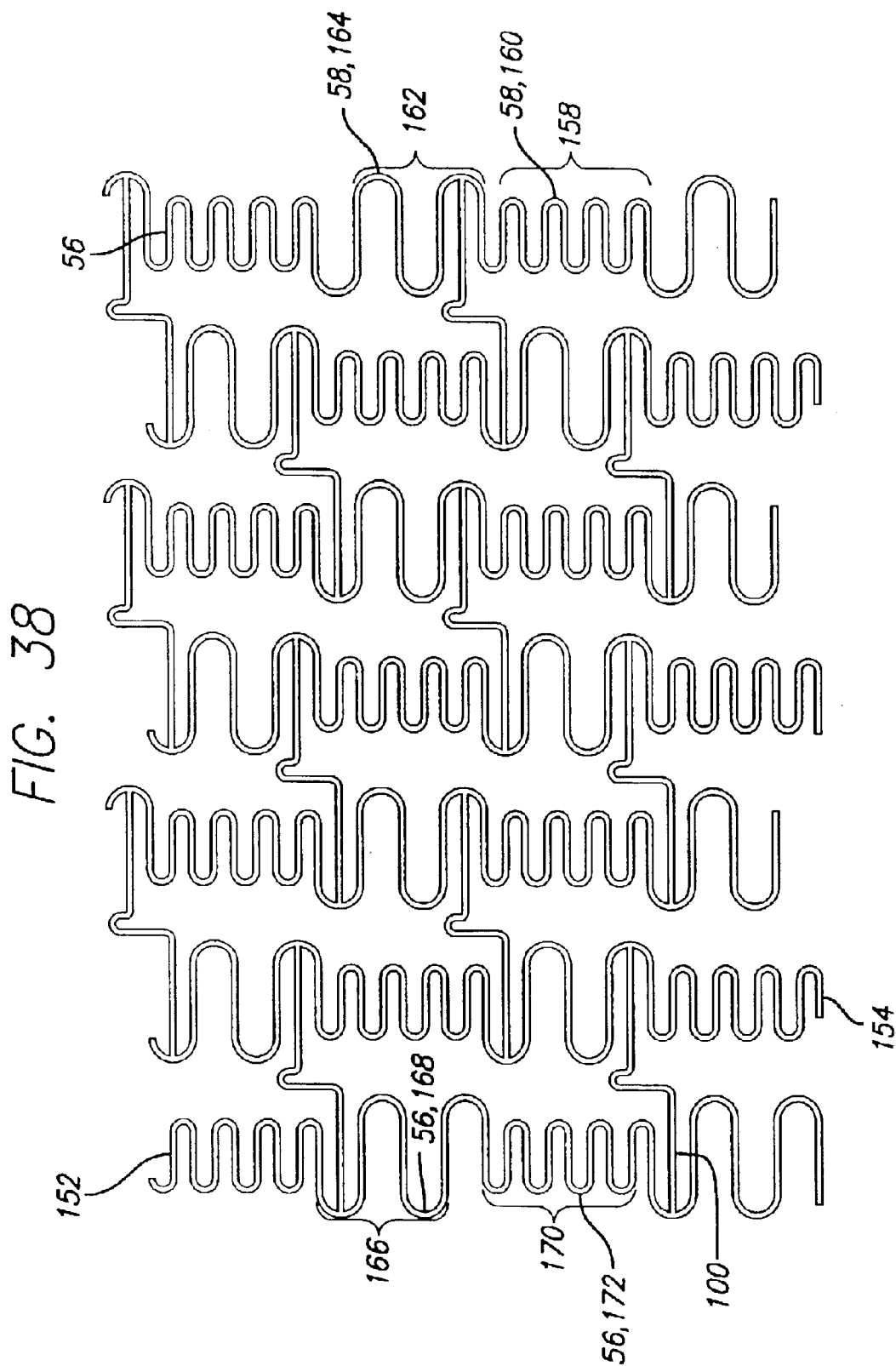
FIG. 38 is a plan view of a flattened stent of the invention which illustrates the pattern of another embodiment of the stent.
Figure 39:
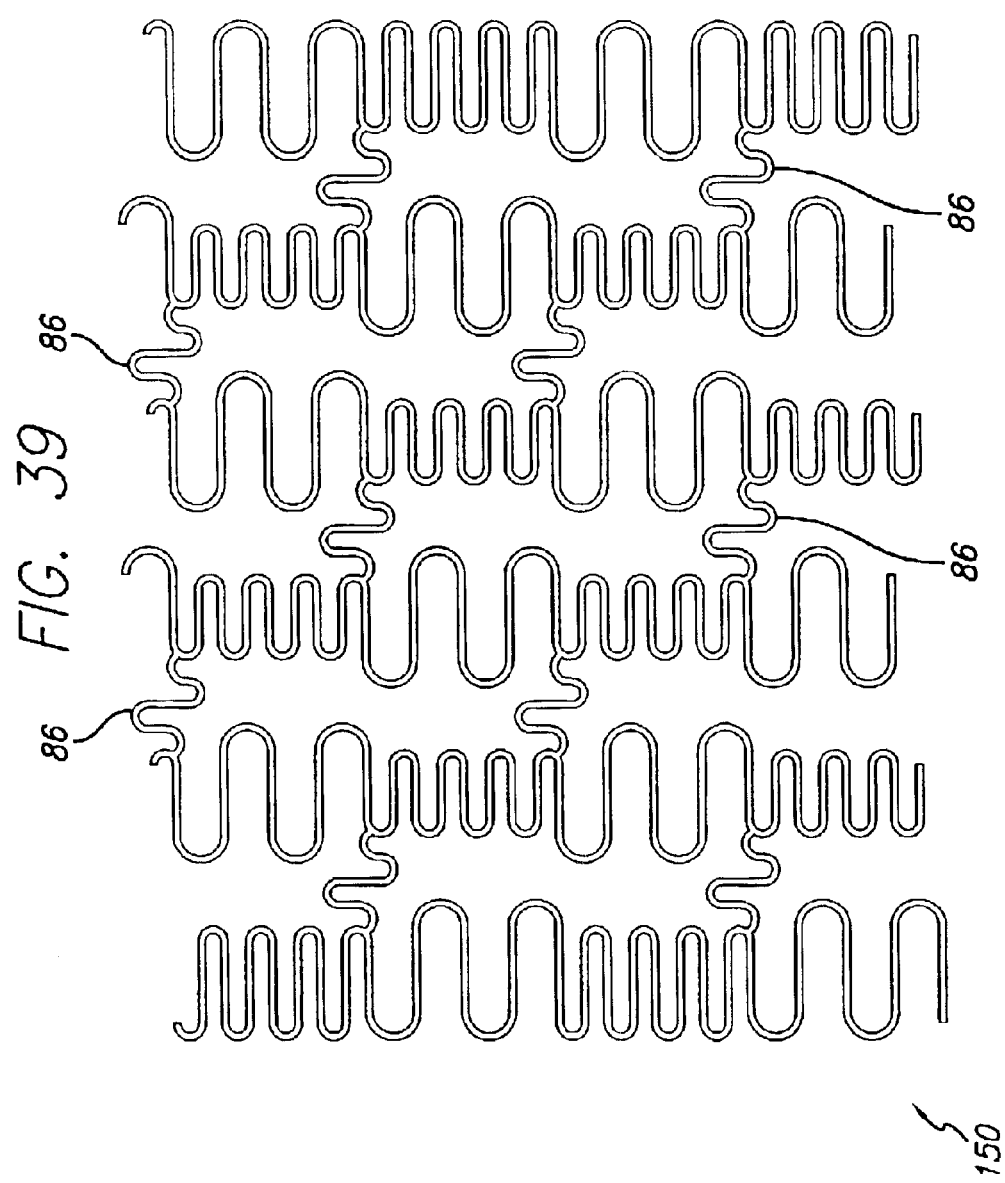
FIG. 39 is a plan view of a flattened stent of the invention which illustrates the pattern of another embodiment of the stent.
Figure 40:
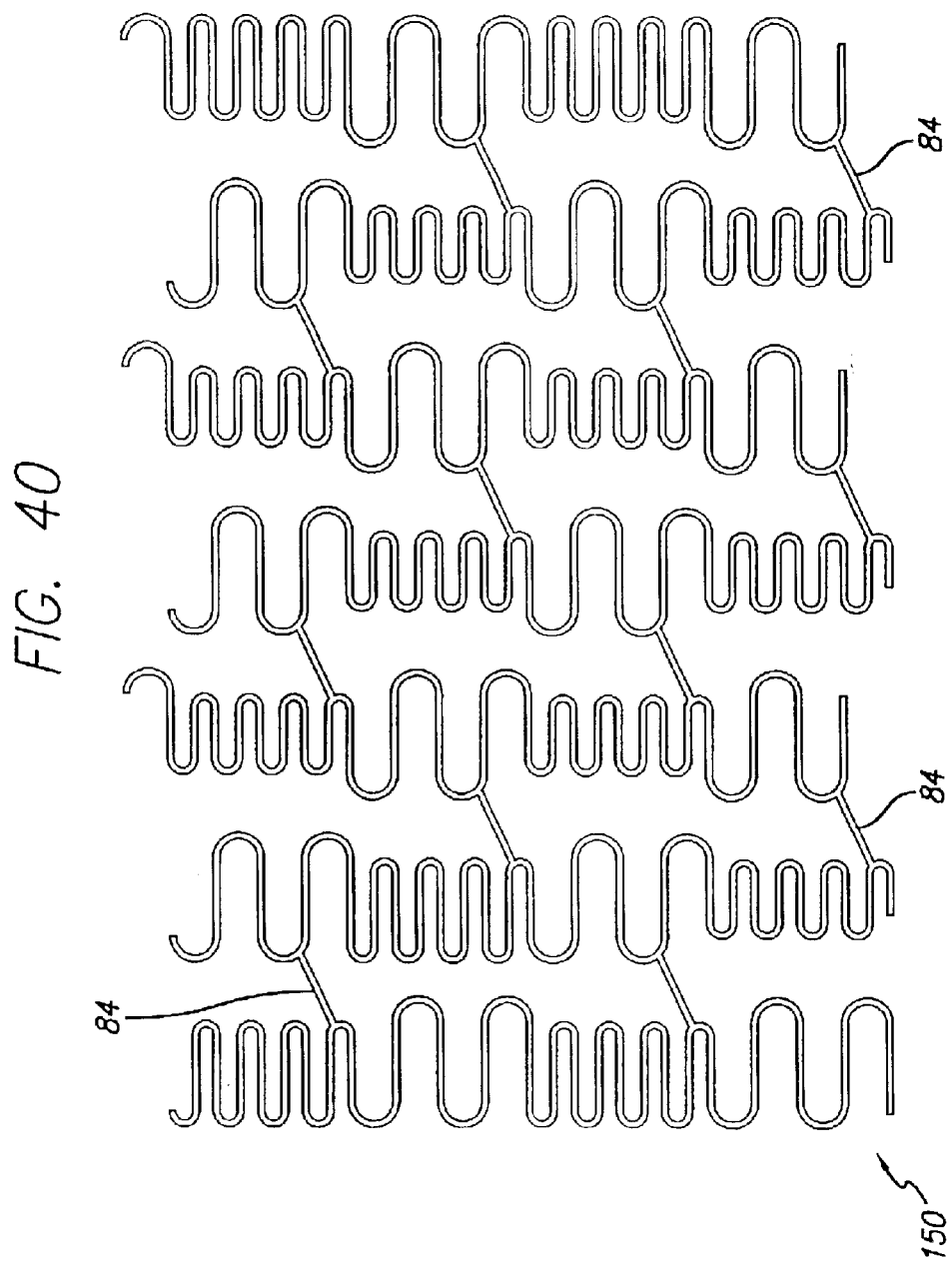
FIG. 40 is a plan view of a flattened stent of the invention which illustrates the pattern of another embodiment of the stent.

Referring to FIG. 38, the first, proximal ring 152 of the stent 150 may include at least one group 166 of adjacent peaks 56 at a first, proximal position 168 along the longitudinal axis of the stent and at least one group 170 of adjacent peaks at a second, more distal position 172 along the longitudinal axis of the stent. Similarly, the strut pattern of the second, distal ring 156 of the stent 150 may include at least one group 158 of adjacent valleys 58 at a first, proximal position 160 along the longitudinal axis of the stent and at least one group 162 of adjacent valleys at a second, more distal position 164 along the longitudinal axis of the stent. In one embodiment (FIG. 39) of the stent 150, at least one of the links 54 may include at least one curved portion, such as the undulating link 86, or the link 100 having at least one curved portion and straight portions. In another embodiment (FIG. 40), the stent 150 may include at least one link 84 having a straight configuration.

The patterns of the stents depicted in FIGS. 4, 16, 17, 27, 37, 38, 39 and 40 provide good vessel conformity due to a short interval for the repetition of the link patterns along the length of the stent. More particularly, the patterns depicted in these figures repeat themselves every two cylindrical rings.

Any portion of the disclosed stent can be made from a metal alloy or from a polymer. For example, the cylindrical rings can be made from a metal alloy while the connecting links can be made from a metal alloy or a polymer. Typically, if the links are made from a polymer, the stent will be more longitudinally flexible than if the links were made from a metal alloy.

Exemplary of the metallic material used in forming the cylindrical rings and links of the stent is stainless steel, titanium, nickel titanium, tantalum, gold, cobalt-chromium, platinum, palladium, and iridium. Other metals, metal alloys and polymers may also be used to form the present invention stent.

Exemplary of the biocompatible polymer material used in forming the rings or the links includes the group of polymers consisting of polyurethanes, polyetherurethanes, polyesterurethanes, silicone, thermoplastic elastomer (C-flex), polyether-amide thermoplastic elastomer (Pebax), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (Kraton) and polyester thermoplastic elastomer (Hytrel), polyethylene, PLA, PGA, and PLGA.

The stent of the invention also can be coated with a drug or therapeutic agent 180, as shown in FIGS. 41–42. Further, it is well known that the stent (when made from a metal) may require a primer material coating such as a polymer to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Examples of therapeutic agents or drugs that are suitable for use with the polymeric materials include sirolimus, everolimus, actinomycin D (ActD), taxol, paclitaxel, or derivatives and analogs thereof. Examples of agents include other antiproliferative substances as well as antineoplastic, anti-inflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents that can be combined with the polymeric materials include antiplatelets, anticoagulants, antifibrins, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone. Such therapeutic agents can also be incorporated into the polymeric stent body.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents is known in the art. Furthermore, the calculation of dosages, dosage rates and appropriate duration of treatment are previously known in the art.

Referring again to FIG. 41, it may be desirable to deposit a higher amount of the drug 180 on the links 182 of a stent to improve uniformity of the drug distribution into the vessel wall through the stent region. It may also be desirable to include a higher amount of the drug 180 on the first, proximal 188 and second, distal 190 rings of the stent to reduce the amount of restenosis at the edges of the stent, or for other purposes. Micro depots 184 (FIGS. 43 and 45), such as apertures or indentations, or micro channels 186 (FIGS. 44 and 46) may be positioned along the links (FIGS. 43 and 44), second, distal ring and proximal ring (FIGS. 45 and 46) at the outer surface of the stent to increase the amount of drug deposited onto the stent in those regions.

The stent 10 of the present invention can be made in many ways. One method of making the stent is to cut a tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

After laser cutting the stent pattern the stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. Other electropolishing solutions are well known in the art. The stents may be further treated if desired, for example by applying a biocompatible coating.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys and pseudoelastic alloys. Shape memory alloys are well known and include, but are not limited to, nickel-titanium and nickel/titanium/vanadium. Any of the shape memory alloys can be formed into a tube and laser cut in order to form the pattern of the stent of the present invention. As is well known, the shape memory alloys of the stent of the present invention can include the type known as thermoelastic martensitic transformation, or display stress-induced martensite. Self-expanding stents can be made with such alloys. These types of alloys are well known in the art and need not be further described here.

Importantly, a stent formed of shape memory alloys, whether the thermoelastic or the stress-induced martensite-type, can be delivered using a balloon catheter of the type described herein, or in the case of a self-expanding stent, such as one made from stress induced martensite, be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of peaks per ring, materials used, and the like have been described herein and are provided as examples only. Other modifications and improvements may be made without departing from the scope of the invention.

What is claimed:

1. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternating between a first, longer ring length and a second, shorter ring length, the cylindrical rings of the first, longer ring length having fewer peaks and valleys than the cylindrical rings of the second, shorter ring length;

the cylindrical rings of the first, longer ring length being in phase with each other;

the cylindrical rings of the second, shorter ring length being in phase with each other, and each cylindrical ring of the second, shorter ring length having a uniform ring length;

at least one peak on each of the cylindrical rings of the second, shorter ring length is coupled to a circumferentially aligned peak on the distally adjacent cylindrical ring of the first, longer ring length by a link; and wherein at least one valley on the cylindrical rings of the first, longer ring length is coupled to a circumferentially aligned valley on the distally adjacent cylindrical ring of the second, shorter ring length by a link.

2. The stent of claim 1, wherein at least one valley on each of the cylindrical rings of the second, shorter ring length is coupled to a circumferentially aligned valley on the distally adjacent cylindrical ring of the first, longer ring length by a link.

3. The stent of claim 1, wherein an undulating link couples at least one valley at the first, proximal position on at least one of the cylindrical rings of the second, shorter length to the circumferentially aligned peak at the second, more distal position on the distally adjacent cylindrical ring of the first, longer length.

4. The stent of claim 1, wherein at least one of the links includes a straight configuration.

5. The stent of claim 1, wherein:

the strut pattern of the cylindrical rings of the first, longer ring length includes a first width;

the strut pattern of the cylindrical rings of the second, shorter ring length includes a second width; and the first strut pattern width is greater than the second strut pattern width, the ratio between the first and second strut pattern widths being within a range of about 1.10:1 to about 1.45:1.

6. The stent of claim 1, wherein the ratio between the first, longer ring length and the second, shorter ring length is within a range of about 1.1:1 to about 1.4:1.

7. The stent of claim 1, wherein the ratio between the first, longer ring length and the second, shorter ring length is within a range of about 1.6:1 to about 2.5:1.

8. The stent of claim 1, wherein the first, longer ring length is within a range of about 0.6 to about 2.0 mm (0.024 0.079 inch) and the second, shorter ring length is within a range of about 0.4 to about 1.2 mm (0.016 0.047 inch).

9. The stent of claim 1, wherein the radial thickness of the stent is variable along the length of the stent.

10. The stent of claim 9, wherein the cylindrical rings of the first, longer ring length include a first radial thickness which is greater than a second radial thickness of the cylindrical rings of the second, shorter ring length.

11. The stent of claim 1, wherein at least one of the peaks of at least one of the cylindrical rings is circumferentially offset and near to a valley on the proximally adjacent cylindrical ring.

12. An intravascular stent for use in a body lumen, comprising:

a plurality of cylindrical rings, each cylindrical ring having a strut pattern, a first, proximal end and a second, distal end the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first proximal end of the cylindrical ring and valleys at the second, distal end of the cylindrical ring with struts extending therebetween;

adjacent cylindrical rings alternating between a first, longer ring length and a second, shorter ring length, the cylindrical rings of the first, longer ring length having fewer peaks and valleys than the cylindrical rings of the second, shorter ring length;

the cylindrical rings of the first, longer ring length being in phase with each other;

the cylindrical rings of the second, shorter ring length being in phase with each other, and each cylindrical ring of the second, shorter ring length having a uniform ring length; and wherein at least one valley on the cylindrical rings of the first, longer ring length is coupled to a circumferentially aligned valley on the distally adjacent cylindrical ring of the second, shorter ring length by a link; and wherein at least one valley on each of the cylindrical rings of the second, shorter ring length is coupled to a circumferentially aligned peak on the distally adjacent cylindrical ring of the first, longer ring length by a link.

13. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternating between a first, longer ring length and a second, shorter ring length, the cylindrical rings of the first, longer ring length having fewer peaks and valleys than the cylindrical rings of the second, shorter ring length;

the cylindrical rings of the first, longer ring length being in phase with each other;

the cylindrical rings of the second, shorter ring length being in phase with each other, and each cylindrical ring of the second, shorter ring length having a uniform ring length; and wherein at least one valley on the cylindrical rings of the first, longer ring length is coupled to a circumferentially aligned valley on the distally adjacent cylindrical ring of the second, shorter ring length by a link; and the cylindrical rings of the second, shorter ring length each include peaks at a first, proximal position and at least one peak at a second, more distal position along the longitudinal axis of the stent; and the at least one peak at the second, more distal position of each of the cylindrical rings of the second, shorter ring length is circumferentially aligned with a valley on the proximally adjacent cylindrical ring of the first, longer ring length.

14. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternating between a first, longer ring length and a second, shorter ring length, the cylindrical rings of the first, longer ring length having fewer peaks and valleys than the cylindrical rings of the second, shorter ring length;

the cylindrical rings of the first, longer ring length being in phase with each other;

the cylindrical rings of the second, shorter ring length being in phase with each other, and each cylindrical ring of the second, shorter ring length having a uniform ring length; and wherein at least one valley on the cylindrical rings of the first, longer ring length is coupled to a circumferentially aligned valley on the distally adjacent cylindrical ring of the second, shorter ring length by a link; and wherein at least one of the links includes straight portions and at least one curved portion.

15. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternating between a first, longer ring length and a second, shorter ring length, the cylindrical rings of the first, longer ring length having fewer peaks and valleys than the cylindrical rings of the second, shorter ring length;

the cylindrical rings of the first, longer ring length being in phase with each other;

the cylindrical rings of the second, shorter ring length being in phase with each other, and each cylindrical ring of the second, shorter ring length having a uniform ring length; and wherein at least one valley on the cylindrical rings of the first, longer ring length is coupled to a circumferentially aligned valley on the distally adjacent cylindrical ring of the second, shorter ring length by a link; and wherein the peaks of each cylindrical ring are circumferentially offset from the valleys on the proximally adjacent cylindrical ring.

16. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternate between a first, longer ring length and a second, shorter ring length, the cylindrical rings of the first, longer ring length having fewer peaks and valleys than the cylindrical rings of the second, shorter ring length;

at least one valley on the cylindrical rings of the first, longer ring length is coupled to a circumferentially aligned valley on the distally adjacent cylindrical ring of the second, shorter ring length by a link; and wherein the peaks of each cylindrical ring are circumferentially offset from and near to the valleys on the proximally adjacent cylindrical ring.

17. The stent of claim 16, wherein:

the circumferential distance between adjacent peaks on at least one of the cylindrical rings is variable about the circumference of the cylindrical rings; and the circumferential distance between adjacent valleys on at least one of the cylindrical rings is variable about the circumference of the cylindrical rings.

18. The stent of claim 16, wherein at least one of the links includes at least one curved portion.

19. The stent of claim 16, wherein at least one peak on at least one cylindrical ring is coupled to a circumferentially offset valley on the proximally adjacent cylindrical ring by a link.

20. An intravascular stent for use in a body lumen, comprising:

a plurality of cylindrical rings including a first, proximal ring, at least one central ring and a second, distal ring, the at least one central ring being positioned between the first, proximal ring and the second, distal ring, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

the strut pattern of the first, proximal ring includes at least one group of adjacent valleys at a first, proximal position along the longitudinal axis of the stent and at least one group of adjacent valleys at a second, more distal position along the longitudinal axis of the stent;

the strut pattern of the at least one central ring includes at least one group of adjacent peaks at a first, proximal position along the longitudinal axis of the stent and at least one group of adjacent peaks at a second, more distal position along the longitudinal axis of the stent;

the strut pattern of the at least one central ring includes at least one group of adjacent valleys at a first, proximal position along the longitudinal axis of the stent and at least one group of adjacent valleys at a second, more distal position along the longitudinal axis of the stent;

the strut pattern of the second, distal ring includes at least one group of adjacent peaks at a first, proximal position along the longitudinal axis of the stent and at least one group of adjacent peaks at a second, more distal position along the longitudinal axis of the stent;

the valleys of the at least one group of adjacent valleys at the first, proximal position of the first, proximal ring are circumferentially aligned with the peaks of the at least one group of adjacent peaks at the first, proximal position of the distally adjacent central ring and the valleys of the at least one group of adjacent valleys at the second, more distal position of the first, proximal ring are circumferentially aligned with the peaks of the at least one group of adjacent peaks at the second, more distal position of the distally adjacent central ring;

wherein the valleys of the at least one group of adjacent valleys at the first, proximal position of the at least one central ring are circumferentially aligned with the peaks of the at least one group of adjacent peaks at the first, proximal position of the distally adjacent cylindrical ring and the valleys of the at least one group of adjacent valleys at the second, more distal position of the at least one central ring are circumferentially aligned with the peaks of the at least one group of adjacent peaks at the second, more distal position of the distally adjacent cylindrical ring;

wherein the number of valleys in the at least one group of adjacent valleys at the first, proximal position of the first, proximal ring is greater than the number of valleys in the at least one group of adjacent valleys at the second, more distal position of the first, proximal ring;

the number of peaks in the at least one group of adjacent peaks at the second, more distal position of the at least one central ring is greater than the number of peaks in the at least one group of adjacent peaks at the first, proximal position of the at least one central ring;

the number of valleys in the at least one group of adjacent valleys at the first, proximal position of the at least one central ring is greater than the number of valleys in the at least one group of adjacent valleys at the second, more distal position of the at least one central ring; and the number of peaks in the at least one group of adjacent peaks at the second, more distal position of the second, distal ring is greater than the number of peaks in the at least one group of adjacent peaks at the first, proximal position. of the second, distal ring.

21. The stent of claim 20, wherein:

the circumferential distance between adjacent valleys at the second, more distal position of the first, proximal ring is greater than the circumferential distance between adjacent valleys at the first, proximal position of the first, proximal ring;

the circumferential distance between adjacent peaks at the first, proximal position of the at least one central ring is greater than the circumferential distance between adjacent peaks at the second, more distal position of the at least one central ring;

the circumferential distance between adjacent valleys at the second, more distal position of the at least one central ring is greater than the circumferential distance between adjacent valleys at the first, proximal position of the at least one central ring;

the circumferential distance between adjacent peaks at the first, proximal position of the second, distal ring is greater than the circumferential distance between adjacent peaks at the second, more distal position of the second, distal ring.

22. The stent of claim 20, wherein:

the arc length of the at least one group of adjacent valleys at the first, proximal position of the first, proximal ring is substantially the same as the arc length of the at least one group of adjacent valleys at the second, more distal position of the first, proximal ring;

the arc length of the at least one group of adjacent peaks at the first, proximal position of the at least one central ring is substantially the same as the arc length of the at least one group of adjacent peaks at the second, more distal position of the at least one central ring;

the arc length of the at least one group of adjacent valleys at the first, proximal position of the at least one central ring is substantially the same as the arc length of the at least one group of adjacent valleys at the second, more distal position of the at least one central ring; and the arc length of the at least one group of adjacent peaks at the first, proximal position of the second, distal ring is substantially the same as the arc length of the at least one group of adjacent peaks at the second, more distal position of the second, distal ring.

23. The stent of claim 20, wherein:

the peaks of the at least one group of adjacent peaks at the first, proximal position of the at least one central ring are circumferentially aligned with the valleys of the at least one group of adjacent valleys at the second, more distal position of the at least one central ring; and the peaks of the at least one group of adjacent peaks at the second, more distal position of the at least one central ring are circumferentially aligned with the valleys of the at least one group of adjacent valleys at the first, proximal position of the at least one central ring.

24. The stent of claim 20, wherein the strut pattern of the first, proximal ring includes at least one group of adjacent peaks at a first, proximal position along the longitudinal axis of the stent and at least one group of adjacent peaks at a second, more distal position along the longitudinal axis of the stent.

25. The stent of claim 20, wherein the strut pattern of the second, distal ring includes at least one group of adjacent valleys at a first, proximal position along the longitudinal axis of the stent and at least one group of adjacent valleys at a second, more distal position along the longitudinal axis of the stent.

26. The stent of claim 20, wherein at least one of the links includes at least one curved portion.

27. The stent of claim 20, wherein at least one of the links includes a straight configuration.

28. The stent of claim 20, wherein at least one of the peaks of at least one of the cylindrical rings is circumferentially offset and near to a valley on the proximally adjacent cylindrical ring.

29. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternate between a first, longer ring length and a second, shorter ring length, the cylindrical rings of the first, longer ring length having fewer peaks and valleys than the cylindrical rings of the second, shorter ring length;

the radial thickness of the stent is variable along the length of the stent;

the cylindrical rings of the first, longer ring length are out of phase with each other;

the cylindrical rings of the second, shorter ring length each include peaks at a first, proximal position and at least one peak at a second, more distal position along the longitudinal axis of the stent, the at least one peak at the second, more distal position of each of the cylindrical rings of the second, shorter ring length is circumferentially aligned with a valley on the proximally adjacent cylindrical ring of the first, longer ring length;

the cylindrical rings of the second, shorter ring length each include at least one valley at a first, proximal position and valleys at a second, more distal position along the longitudinal axis of the stent, the at least one valley at the first, proximal position of each of the cylindrical rings of the second, shorter ring length is circumferentially aligned with a peak on the distally adjacent cylindrical ring of the first, longer ring length; and wherein at least one valley on the cylindrical rings of the first, longer ring length is coupled to a circumferentially aligned valley on the distally adjacent cylindrical ring of the second, shorter ring length by a link.

30. The stent of claim 29, wherein the cylindrical rings of the first, longer ring length include a first radial thickness which is greater than a second radial thickness of the cylindrical rings of the second, shorter ring length.

31. The stent of claim 29, wherein at least one of the peaks of at least one of the cylindrical rings is circumferentially offset and near to a valley on the proximally adjacent cylindrical ring.

32. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternating between a first, longer ring length and a second, shorter ring length, the cylindrical rings of the first, longer ring length having fewer peaks and valleys than the cylindrical rings of the second, shorter ring length;

the cylindrical rings of the first, longer ring length being in phase with each other;

the cylindrical rings of the second, shorter ring length being in phase with each other;

wherein at least one valley on the cylindrical rings of the first, longer ring length is coupled to a circumferentially aligned valley on the distally adjacent cylindrical ring of the second, shorter ring length by a link; and wherein at least one peak on each of the cylindrical rings of the second, shorter ring length is coupled to a circumferentially aligned valley on the distally adjacent cylindrical ring of the first, longer ring length by a link.

33. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternating between a first, longer ring length and a second, shorter ring length, the cylindrical rings of the first, longer ring length having fewer peaks and valleys than the cylindrical rings of the second, shorter ring length;

the cylindrical rings of the first, longer ring length being in phase with each other;

the cylindrical rings of the second, shorter ring length being in phase with each other;

wherein at least one valley on the cylindrical rings of the first, longer ring length is coupled to a circumferentially aligned valley on the distally adjacent cylindrical ring of the second, shorter ring length by a link; and wherein at least one valley on at least one cylindrical ring of the second, shorter ring length is coupled to a circumferentially offset peak on the distally adjacent cylindrical ring of the first, longer ring length by a link.

34. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternating between a first, longer ring length and a second, shorter ring length, the cylindrical rings of the first, longer ring length having fewer peaks and valleys than the cylindrical rings of the second, shorter ring length;

the cylindrical rings of the first, longer ring length being in phase with each other;

the cylindrical rings of the second, shorter ring length being in phase with each other;

wherein at least one valley on the cylindrical rings of the first, longer ring length is coupled to a circumferentially aligned valley on the distally adjacent cylindrical ring of the second, shorter ring length by a link;

wherein the cylindrical rings of the second, shorter ring length each include at least one valley at a first, proximal position and valleys at a second, more distal position along the longitudinal axis of the stent; and wherein the at least one valley at the first, proximal position of each of the cylindrical rings of the second, shorter ring length is circumferentially aligned with a peak on the distally adjacent cylindrical ring of the first, longer ring length.

35. An intravascular stent for use in a body lumen, comprising:

a plurality of cylindrical rings, each cylindrical ring having a strut pattern, a first, proximal end and a second, distal end, the first, proximal end and the second, distal end defining a ring length, the cylindrical rings being aligned along a common longitudinal axis of the stent and radially expandable with a first delivery diameter and a second implanted diameter; and at least one link coupling each pair of adjacent cylindrical rings;

wherein the strut pattern of each cylindrical ring includes an undulating pattern of U shaped portions forming peaks at the first, proximal end of the cylindrical ring and valleys at the second, distal end of the cylindrical ring with struts extending therebetween;

adjacent cylindrical rings alternating between a first, longer ring length and a second, shorter ring length, the cylindrical rings of the first, longer ring length having fewer peaks and valleys than the cylindrical rings of the second, shorter ring length;

the cylindrical rings of the first, longer ring length being in phase with each other;

the cylindrical rings of the second, shorter ring length being in phase with each other;

wherein at least one valley on the cylindrical rings of the first, longer ring length is coupled to a circumferentially aligned valley on the distally adjacent cylindrical ring of the second, shorter ring length by a link; and wherein at least one of the links includes an undulating configuration.

* * * * *